(12) United States Patent
Yamauchi et al.

(10) Patent No.: US 12,277,763 B2
(45) Date of Patent: Apr. 15, 2025

(54) LOAD ESTIMATION APPARATUS AND METHOD

(71) Applicant: KABUSHIKI KAISHA TOSHIBA, Tokyo (JP)

(72) Inventors: Yasunobu Yamauchi, Yokohama Kanagawa (JP); Tsukasa Ike, Tokyo (JP); Izumi Fukunaga, Tokyo (JP); Akiyuki Tanizawa, Kawasaki Kanagawa (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 788 days.

(21) Appl. No.: 17/463,107

(22) Filed: Aug. 31, 2021

(65) Prior Publication Data
US 2022/0138471 A1 May 5, 2022

(30) Foreign Application Priority Data
Nov. 4, 2020 (JP) .................................. 2020-184609

(51) Int. Cl.
G06V 20/40 (2022.01)
A61B 5/11 (2006.01)
G06T 7/246 (2017.01)

(52) U.S. Cl.
CPC ............ G06V 20/41 (2022.01); A61B 5/1116 (2013.01); A61B 5/1121 (2013.01); A61B 5/1128 (2013.01); G06T 7/246 (2017.01); A61B 2562/0219 (2013.01);
(Continued)

(58) Field of Classification Search
CPC . G06T 7/70; G06T 7/246; G06T 2207/30232; G06T 2207/30196; A61B 5/1116; A61B 5/1121; A61B 5/1128; A61B 5/6823; A61B 5/6824; A61B 2562/0219; A61B 2503/20; G06V 10/763;
(Continued)

(56) References Cited

U.S. PATENT DOCUMENTS

2011/0060248 A1 3/2011 Ishida et al.
2014/0326084 A1 11/2014 Bhushan
(Continued)

FOREIGN PATENT DOCUMENTS

JP 2014217753 A 11/2014
JP 2019021051 A 2/2019
(Continued)

OTHER PUBLICATIONS

Sashida et al., WO 2015133206 A1, "Image processing device, image processing method, and image processing program", Date published: Sep. 11, 2015 (Year: 2015).*
(Continued)

*Primary Examiner* — John H Le
(74) *Attorney, Agent, or Firm* — Holtz, Holtz & Volek PC

(57) ABSTRACT

According to one embodiment, a load estimation apparatus includes processing circuitry. The processing circuitry acquires sensor data from a measurement target, calculates one or more posture loads relating to one or more body parts of the measurement target based on the sensor data, and displays display data including a posture load graph in which the one or more posture loads are illustrated in time series.

11 Claims, 28 Drawing Sheets

(52) U.S. Cl.
CPC .............. *G06T 2207/30196* (2013.01); *G06T 2207/30232* (2013.01); *G06V 20/44* (2022.01); *G06V 2201/07* (2022.01)

(58) Field of Classification Search
CPC ...... G06V 20/41; G06V 20/44; G06V 40/107; G06V 2201/07
USPC .......................................................... 702/41
See application file for complete search history.

(56) References Cited

U.S. PATENT DOCUMENTS

| | | | |
|---|---|---|---|
| 2015/0223743 A1* | 8/2015 | Pathangay | A61B 5/18 600/509 |
| 2017/0344919 A1 | 11/2017 | Chang et al. | |
| 2018/0144427 A1* | 5/2018 | Ebesu | G08B 21/06 |
| 2019/0026682 A1 | 1/2019 | Ike et al. | |
| 2022/0082462 A1 | 3/2022 | Sakuragi et al. | |

FOREIGN PATENT DOCUMENTS

| | | |
|---|---|---|
| JP | 2019103609 A | 6/2019 |
| JP | 2019115651 A | 7/2019 |
| JP | 2020140609 A | 9/2020 |
| JP | 2022048014 | 3/2022 |
| WO | 2009116597 A1 | 9/2009 |
| WO | 2017037839 A1 | 3/2017 |

OTHER PUBLICATIONS

Ura Kazuo, JP 2015112392 A, "Exercise Information Display System, Exercise Information Display Method, and Exercise Information Display Program", Date published Jun. 22, 2015 (Year: 2015).*

U.S. Appl. No. 17/461,596, First Named Inventor: Yojiro Tonouchi; Title: "Information Processing Apparatus, Method, and Non-Transitory Computer-Readable Storage Medium"; Filed: Aug. 30, 2021.

* cited by examiner

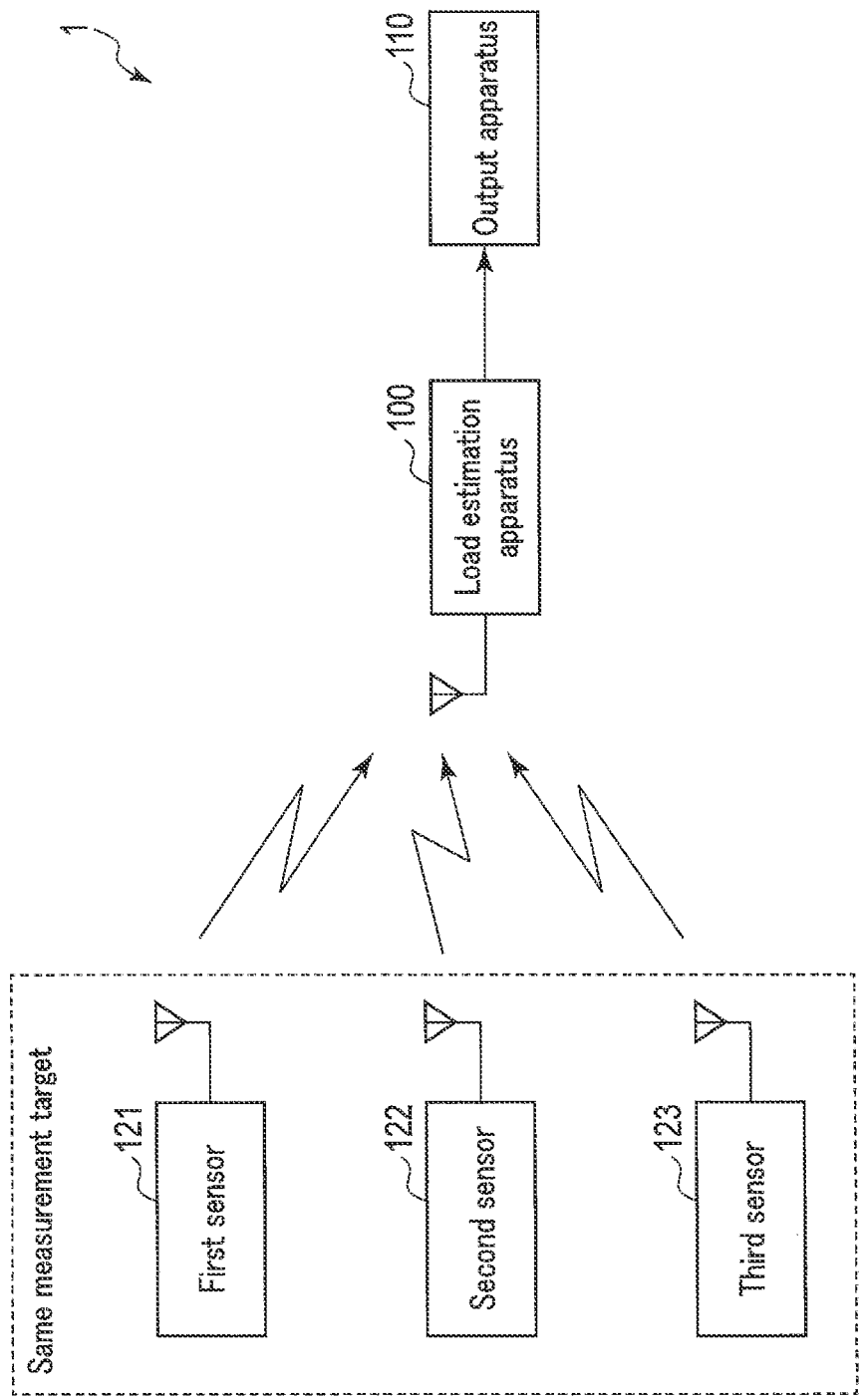
F I G. 1

| Time | Worker ID | Load value (upper arm) | Load value (wrist) | Load value (waist) | Acceleration (X) | Acceleration (Y) | Acceleration (Z) |
|---|---|---|---|---|---|---|---|
| 15:35:17.436 | Heavy manual worker A | 0.10896 | 0.573486 | 0 | 3.639378 | 0.29932 | 9.276312 |
| 15:35:17.446 | Heavy manual worker A | 0.109985 | 0.584398 | 0 | 3.586105 | 0.305522 | 9.30682 |
| 15:35:17.456 | Heavy manual worker A | 0.110903 | 0.595314 | 0 | 3.532437 | 0.311497 | 9.337995 |
| 15:35:17.466 | Heavy manual worker A | 0.111735 | 0.606225 | 0 | 3.478365 | 0.317313 | 9.369766 |
| 15:35:17.476 | Heavy manual worker A | 0.112494 | 0.617143 | 0 | 3.42382 | 0.323221 | 9.402115 |
| 15:35:17.486 | Heavy manual worker A | 0.113188 | 0.628076 | 0 | 3.368747 | 0.329269 | 9.434989 |

F I G. 20

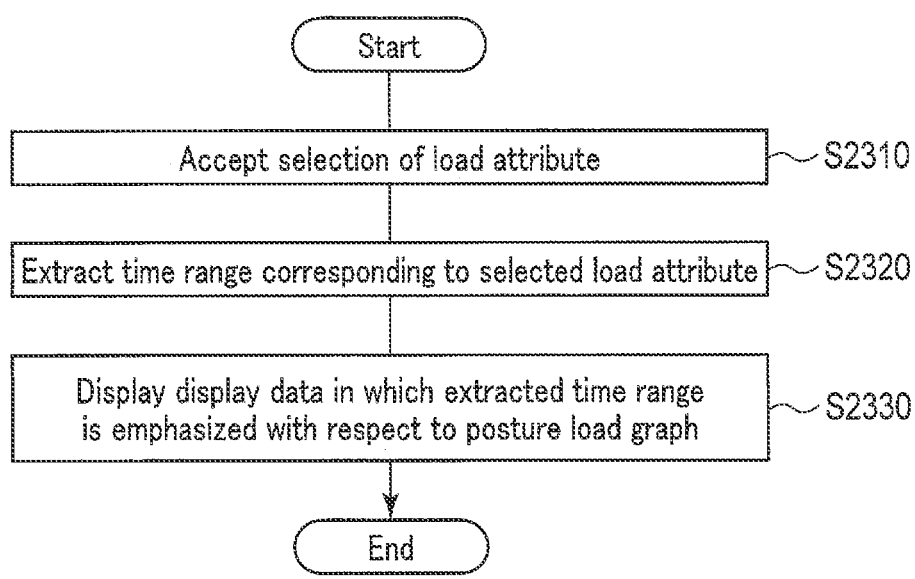
F I G. 23

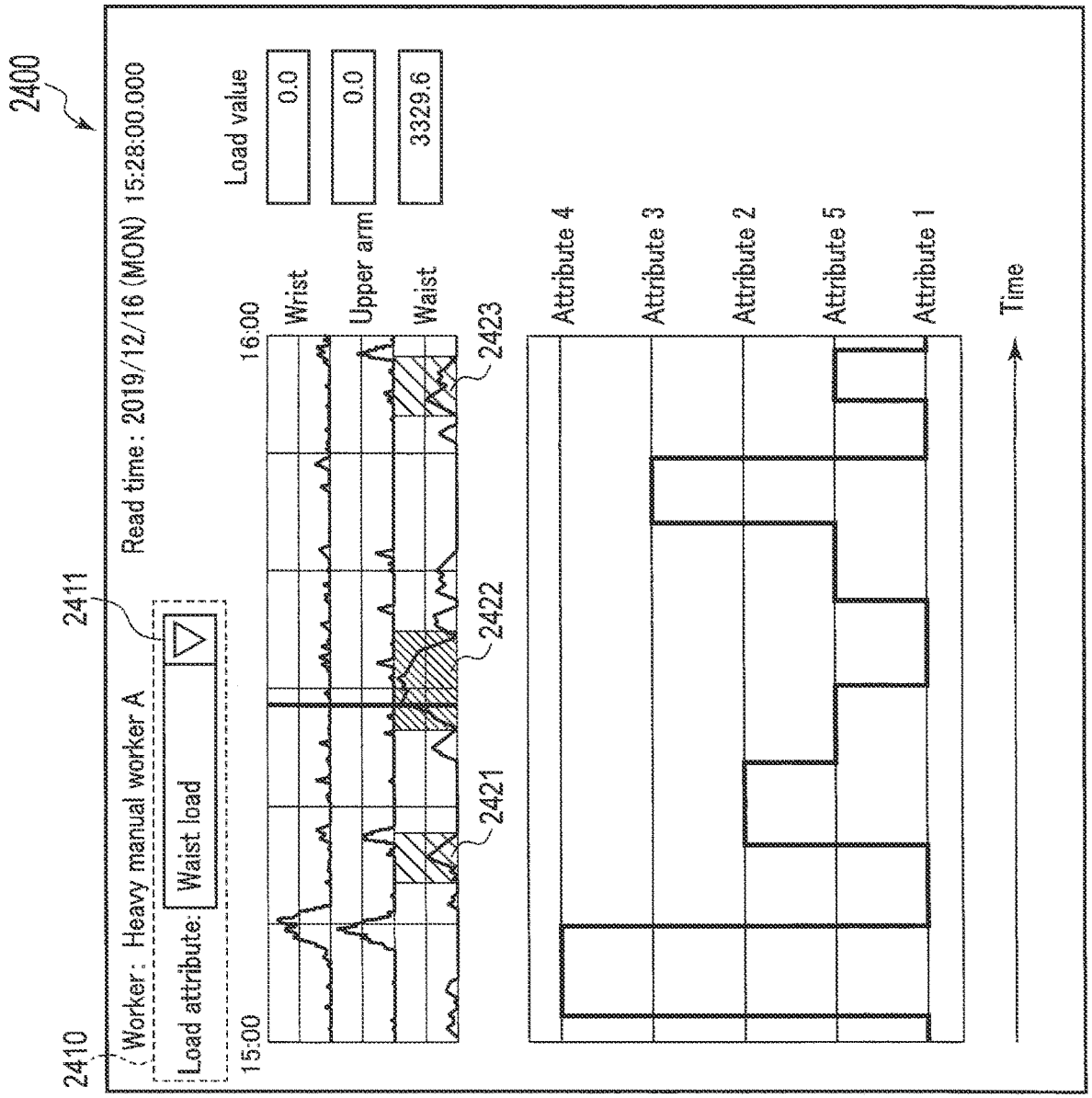
F I G. 24

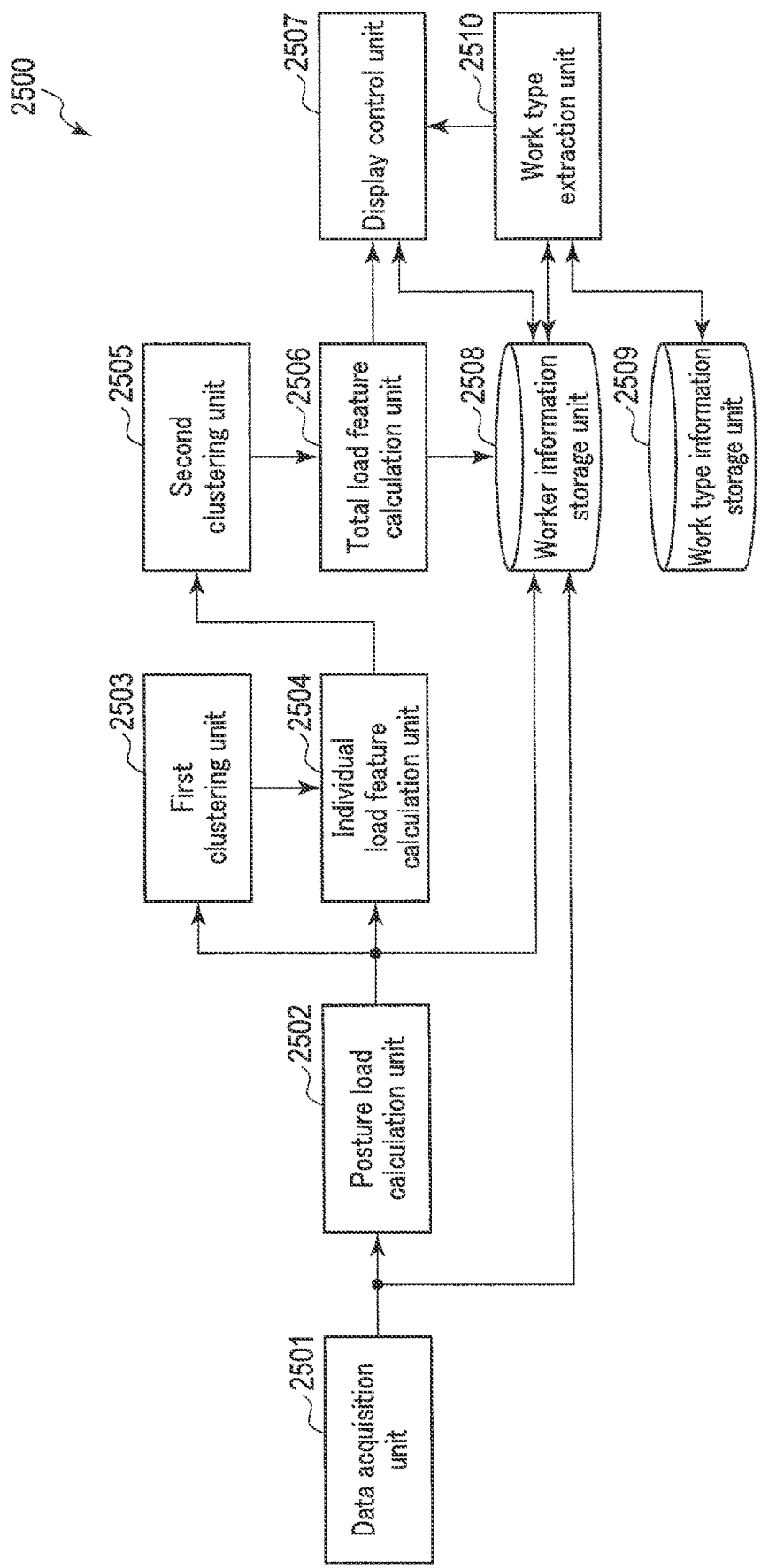
F I G. 25

| Worker ID | Work type | Work period (start) | Work period (end) |
|---|---|---|---|
| Heavy manual worker A | Propeller installation | 15:10:05.432 | 15:10:15.520 |
| Heavy manual worker A | Power supply installation | 15:10:15.520 | 15:10:22.518 |
| Heavy manual worker A | Assembly | 15:10:15.520 | 15:10:22.518 |
| Heavy manual worker A | Walk | 15:10:22.518 | 15:10:23.423 |
| Heavy manual worker A | Small tool work | 15:10:22.518 | 15:10:23.423 |
| Heavy manual worker A | Transport | 15:10:23.423 | 15:10:26.709 |

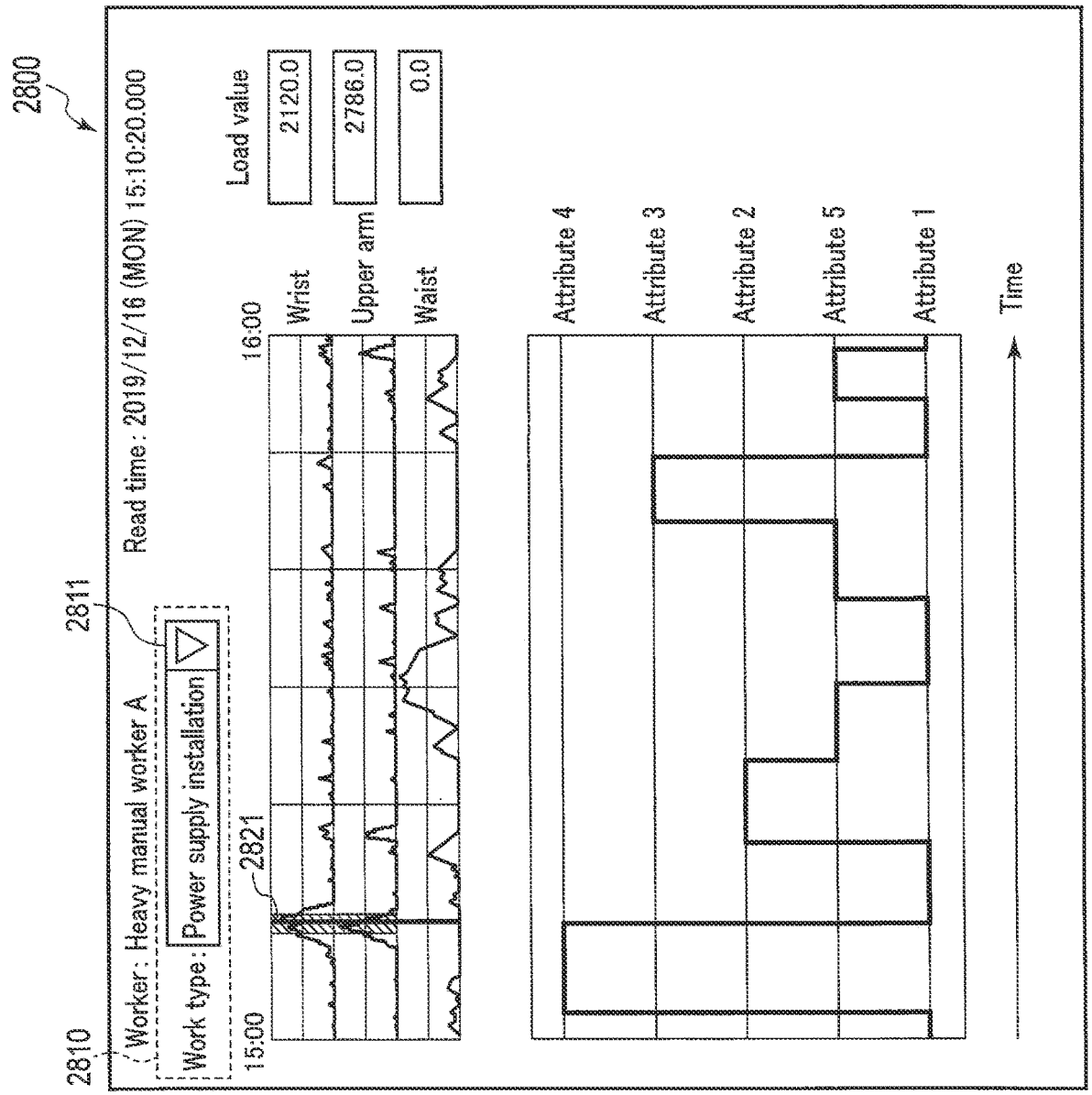
F I G. 28

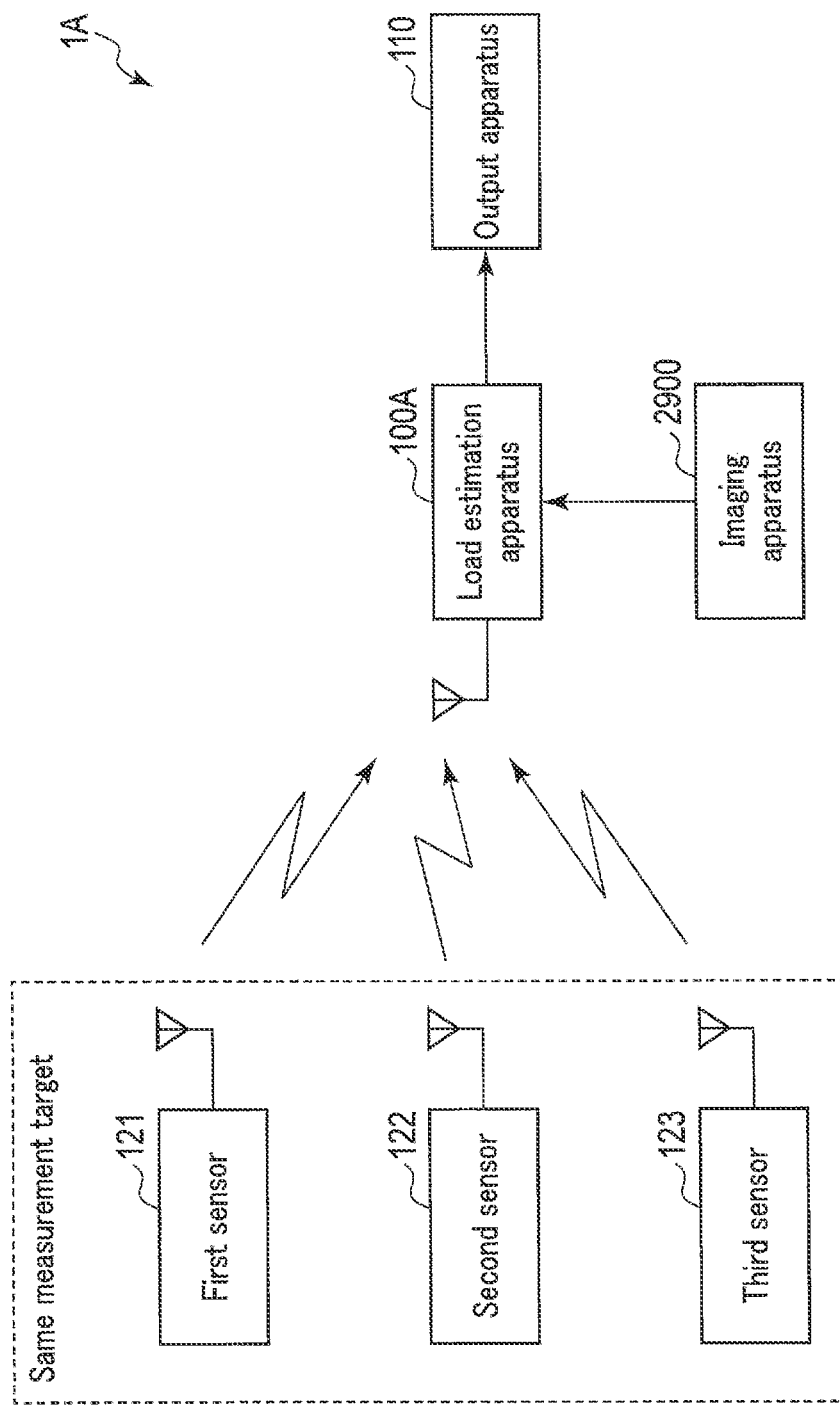
F I G. 29

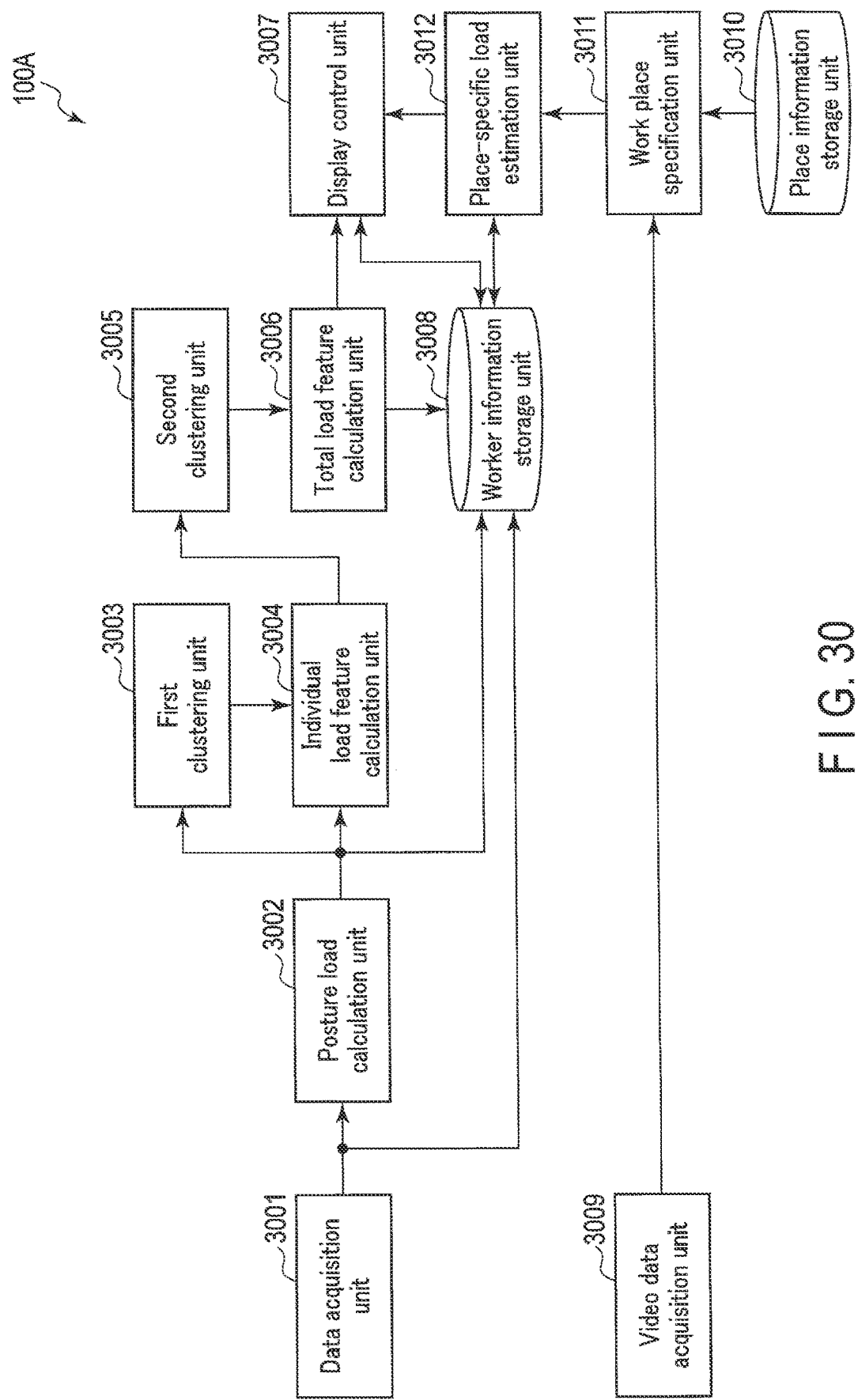
F I G. 30

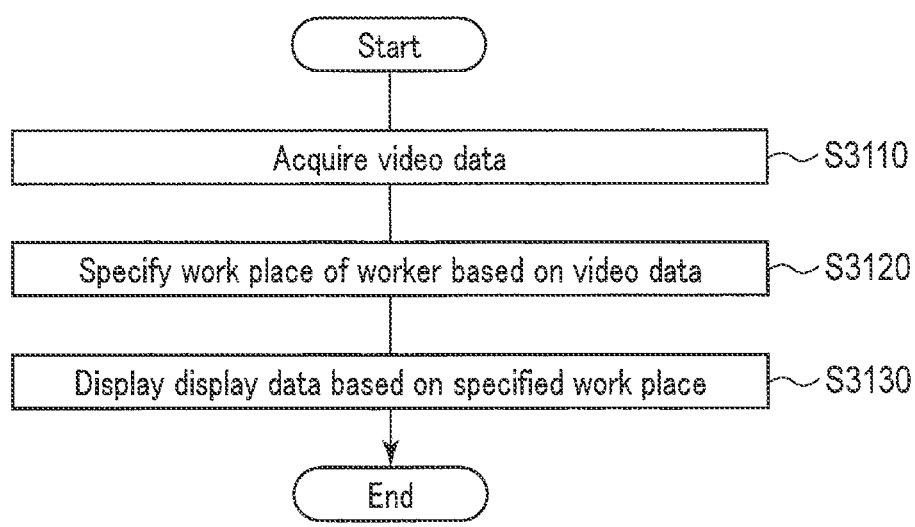
F I G. 31

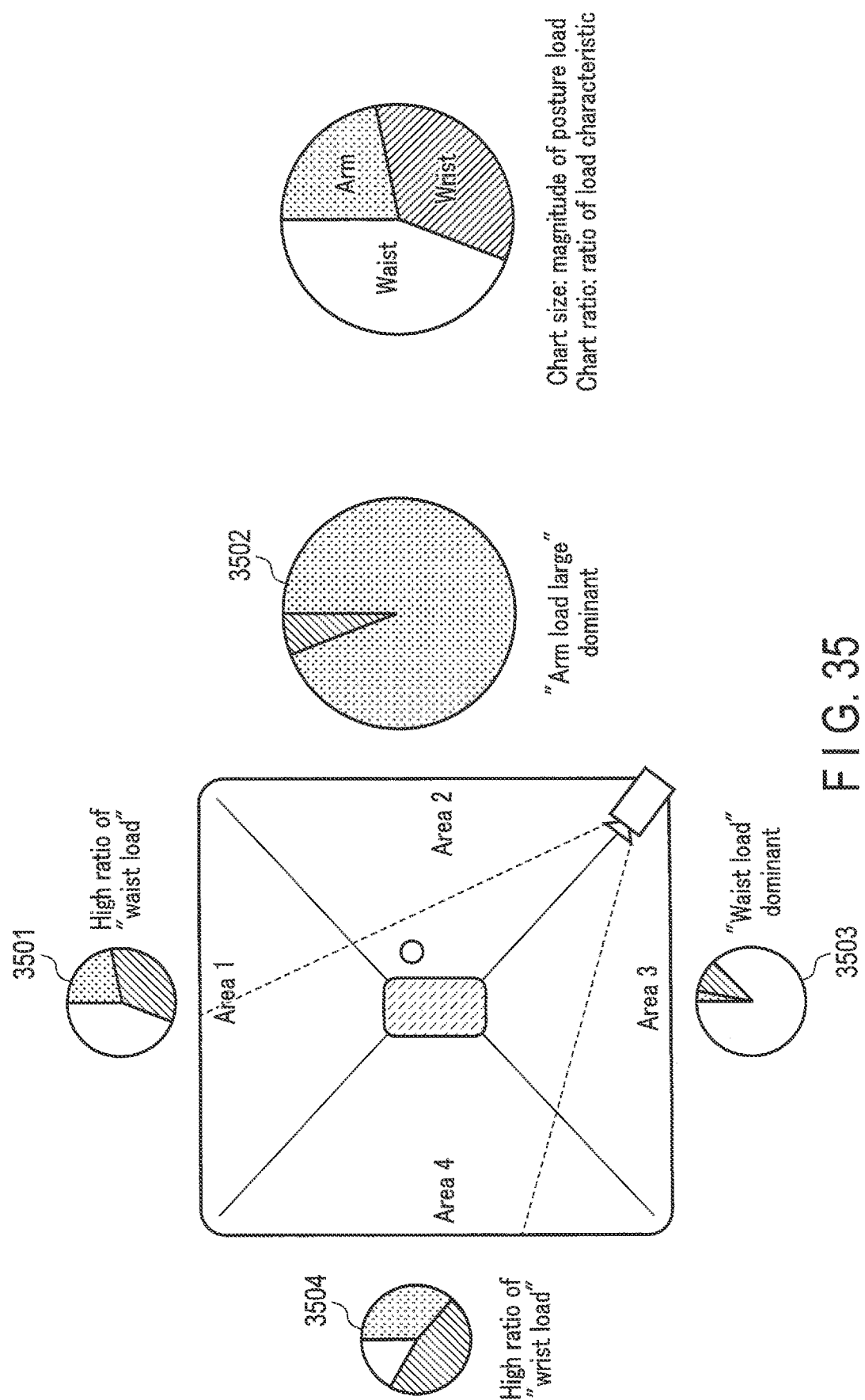
F I G. 35

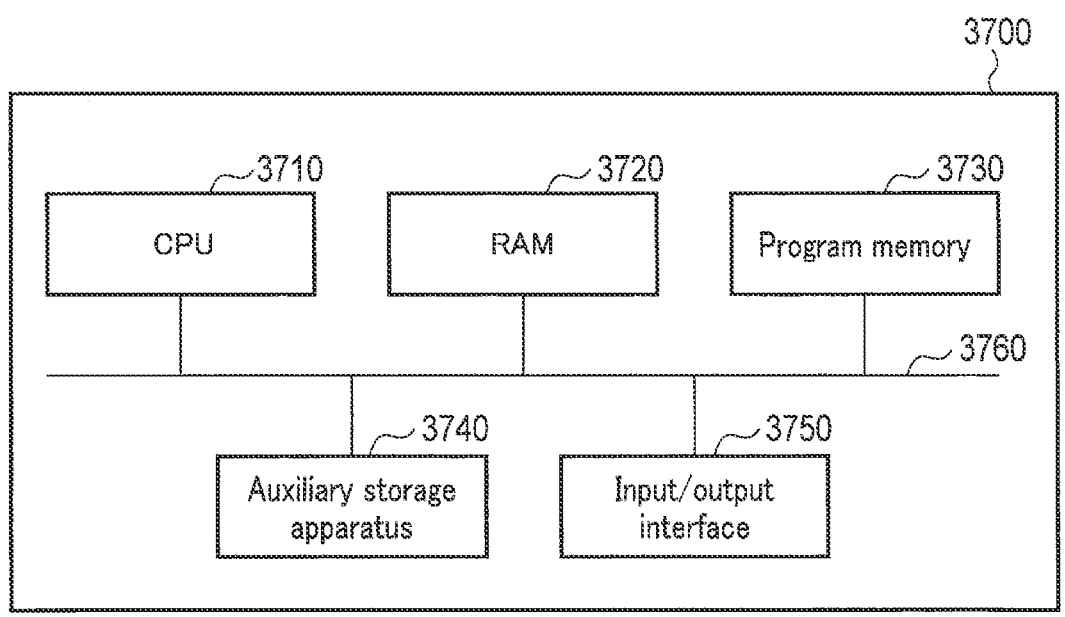
F I G. 37

LOAD ESTIMATION APPARATUS AND METHOD

CROSS-REFERENCE TO RELATED APPLICATIONS

This application is based upon and claims the benefit of priority from Japanese Patent Application No. 2020-184609, filed Nov. 4, 2020, the entire contents of which are incorporated herein by reference.

FIELD

Embodiments described herein relate generally to a load estimation apparatus and a load estimation method.

BACKGROUND

At a manufacturing site, a distribution site, and the like, for example, it is necessary to estimate a load on a worker when a work time and a break time of the worker are allocated. As the worker's load estimation, for example, a method of estimating a load from a work table is known. In this method, it is assumed that the worker works according to a predetermined work table, and the load estimation is performed based on a load value associated with each work included in the work table. However, in this method, since the motion of the worker and the like are not reflected, there is a possibility that the estimated load and the actual load deviate from each other.

In addition, as another load estimation of the worker, a method of estimating a load using a motion sensor is known. In this method, a load is estimated from sensor data acquired by the motion sensor attached to the worker, and a warning is issued in a case where the load becomes equal to or more than a certain level. However, in this method, since the load is estimated by focusing on the duration of the posture of the worker, it is difficult to grasp in which work state the warning is issued. In addition, in this method, since a difference in motion for each worker is not considered, it is not possible to compare loads relating to work motions among workers, and it is also difficult to improve the work motion.

BRIEF DESCRIPTION OF THE DRAWINGS

FIG. 1 is a block diagram illustrating a configuration of a load estimation system including a load estimation apparatus according to a first embodiment;

FIG. 20 is a table in which time, a worker ID, posture load information, and sensor data are associated with each other in the second embodiment;

FIG. 23 is a flowchart illustrating an operation of the load estimation apparatus according to the third embodiment;

FIG. 24 is an example of display data in the third embodiment;

FIG. 25 is a block diagram illustrating a configuration of a load estimation apparatus according to a fourth embodiment;

FIG. 28 is an example of display data in the fourth embodiment;

FIG. 29 is a block diagram illustrating a configuration of a load estimation system including a load estimation apparatus according to a fifth embodiment;

FIG. 30 is a block diagram illustrating a configuration of the load estimation apparatus according to the fifth embodiment;

FIG. 31 is a flowchart illustrating an operation of the load estimation apparatus according to the fifth embodiment;

FIG. 35 is a diagram illustrating pie charts displayed together with a sketch in the fifth embodiment;

FIG. 37 is a block diagram illustrating a hardware configuration of a computer according to an embodiment.

DETAILED DESCRIPTION

Figure 2:
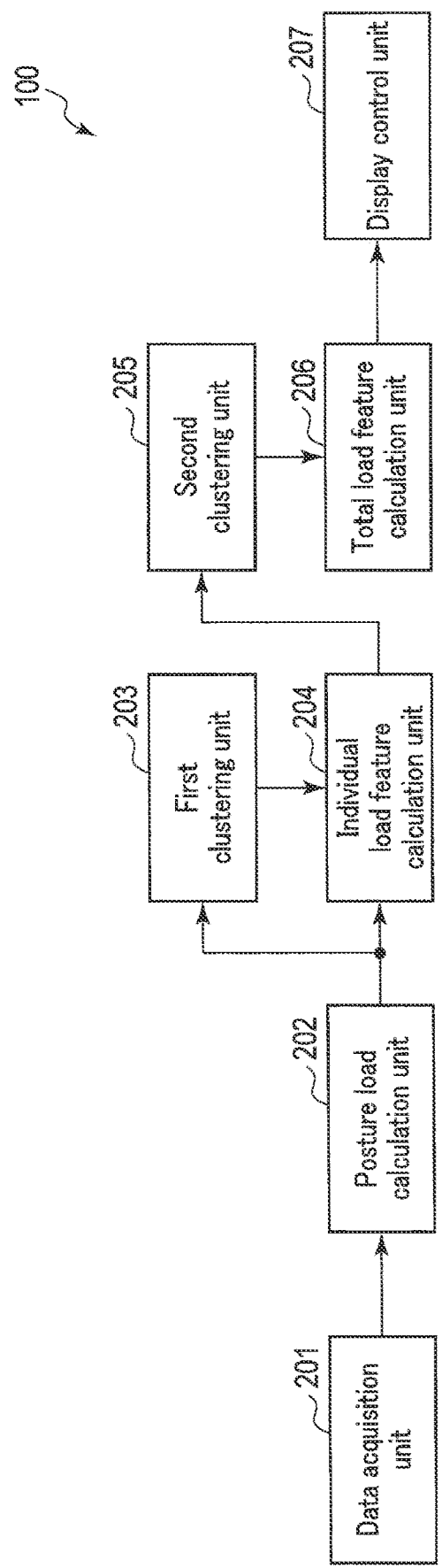
FIG. 2 is a block diagram illustrating a configuration of the load estimation apparatus according to the first embodiment.

In general, according to one embodiment, a load estimation apparatus includes processing circuitry. The processing circuitry acquires sensor data from a measurement target, calculates one or more posture loads relating to one or more body parts of the measurement target based on the sensor data, and displays display data including a posture load graph in which the one or more posture loads are illustrated in time series.

Hereinafter, embodiments of a load estimation apparatus will be described in detail with reference to the drawings.

First Embodiment

FIG. 1 is a block diagram illustrating a configuration of a load estimation system including a load estimation apparatus according to a first embodiment. A load estimation system 1 of FIG. 1 includes a load estimation apparatus 100, an output apparatus 110, and one or more sensors. In FIG. 1, a first sensor 121, a second sensor 122, and a third sensor 123 are illustrated as one or more sensors. Each of these three sensors acquires sensor data for the same measurement target. The measurement target is, for example, a worker who works at a work site such as a factory. The load estimation apparatus 100 estimates a characteristic of a load (load characteristic) relating to work based on one or more pieces of sensor data. The output apparatus 110 displays display data based on the load characteristic.

The load estimation system 1 may include a sensor that acquires sensor data on another measurement target. That is, the load estimation apparatus 100 may acquire one or more pieces of sensor data from each of a plurality of measurement targets.

The output apparatus 110 is, for example, a monitor. The output apparatus 110 receives display data from the load estimation apparatus 100. The output apparatus 110 displays the display data. Note that the output apparatus 110 is not limited to the monitor as long as display data can be displayed. For example, the output apparatus 110 may be a projector and a printer. Furthermore, the output apparatus 110 may include a speaker.

The one or more sensors are incorporated in, for example, wearable devices attached to a plurality of body parts of the measurement target. Hereinafter, the wearable device and the sensor are used in the same meaning. The plurality of body parts are, for example, a wrist, an upper arm, an ankle, a thigh, a waist, a back, a head, and the like. Each of the one or more sensors acquires, as sensor data, at least one piece of measurement data such as acceleration data, angular velocity data, geomagnetic data, atmospheric pressure data, temperature and humidity data, myoelectric potential data, and pulse wave data, for example. Preferably, each sensor acquires at least acceleration data as sensor data. The measurement data may include a plurality of channels. For example, in a case where the measurement data is acceleration data, the sensor data includes measurement data for three channels corresponding to each direction (for example, the X-axis direction, the Y-axis direction, and the Z-axis direction) component of the acceleration. In the present embodiment, a case where the first sensor 121, the second sensor 122, and the third sensor 123 are used as one or more sensors will be described. These sensors are acceleration sensors, for example.

The first sensor 121 is attached to, for example, a wrist of the measurement target. The first sensor 121 measures a state of the wrist of the measurement target as sensor data. The first sensor 121 outputs the measured sensor data to the load estimation apparatus 100.

The second sensor 122 is attached to, for example, an upper arm of the measurement target. The second sensor 122 measures a state of the upper arm of the measurement target as sensor data. The second sensor 122 outputs the measured sensor data to the load estimation apparatus 100.

The third sensor 123 is attached to, for example, the waist of the measurement target. The third sensor 123 measures a state of the waist of the measurement target as sensor data. The third sensor 123 outputs the measured sensor data to the load estimation apparatus 100.

FIG. 2 is a block diagram illustrating a configuration of the load estimation apparatus according to the first embodiment. The load estimation apparatus 100 of FIG. 2 includes a data acquisition unit 201, a posture load calculation unit 202, a first clustering unit 203 (first generation unit), an individual load feature calculation unit 204, a second clustering unit 205 (second generation unit), a total load feature calculation unit 206, and a display control unit 207.

The data acquisition unit 201 acquires sensor data from each of the first sensor 121, the second sensor 122, and the third sensor 123. Hereinafter, in a case where it is not necessary to distinguish these three pieces of sensor data, the pieces of sensor data are simply referred to as sensor data. The data acquisition unit 201 outputs the acquired sensor data to the posture load calculation unit 202. The sensor data includes, for example, data in which time and measurement data for three channels of each sensor are associated with each other. Note that the data acquisition unit 201 may store the acquired sensor data in a storage unit (not illustrated in FIG. 2) or may transmit the acquired sensor data to an external server.

The posture load calculation unit 202 receives sensor data from the data acquisition unit 201. The posture load calculation unit 202 calculates a posture load based on the sensor data. The posture load calculation unit 202 outputs information on the calculated posture load (posture load information) to each of the first clustering unit 203 and the individual load feature calculation unit 204. Note that the posture load calculation unit 202 may store the calculated posture load information in the storage unit or may transmit the calculated posture load information to an external server.

The posture load information includes, for example, data in which time and a posture load relating to a part corresponding to each sensor are associated with each other. The posture load is a load in a work posture that can cause a physical load. Therefore, depending on the worker's posture, there may be a time at which the posture load information is not calculated. The posture load information may include a posture load of a part corresponding to at least one sensor. Hereinafter, a combination of a certain time and a posture load of each part corresponding to the time may be referred to as a "sample". That is, the posture load information includes a plurality of samples. The number of the plurality of samples is determined by a period for acquiring the sensor data and a sampling cycle for acquiring the sensor data. The sampling cycle is, for example, 10 msec. Note that a sample ID for specifying an individual sample may be assigned to each of the plurality of samples.

Specifically, the posture load calculation unit 202 calculates a posture angle based on the sensor data. More specifically, the posture load calculation unit 202 calculates, for example, an angle formed by a vector in the gravity direction estimated from the acceleration component and the reference axis of the attached sensor, as the posture angle. Alternatively, the posture load calculation unit 202 may calculate the posture angle by using a learned model of machine learning learned to output the posture angle when the sensor data is input.

Furthermore, the posture load calculation unit 202 performs a standardization process on the calculated posture angle, and calculates a standard posture angle. Then, the posture load calculation unit 202 generates a posture angle distribution using the calculated standard posture angle, performs a threshold process using the generated posture angle distribution, and calculates the posture load.

The first clustering unit 203 receives posture load information from the posture load calculation unit 202. The first clustering unit 203 performs first clustering using the posture load information, and generates a first clustering result. The first clustering unit 203 outputs the generated first clustering result to the individual load feature calculation unit 204.

As a clustering method, for example, k-means clustering is used. Alternatively, any method such as hierarchical clustering or density-based spatial clustering of application with noise (DBSCAN) may be used. The same applies to second clustering described later.

The first clustering result includes data in which a sample ID and a cluster ID (first cluster ID) for distinguishing each cluster in the first clustering are associated with each other. Furthermore, the first clustering result includes information on a representative sample in each cluster. The representative sample corresponds to, for example, an average sample among the samples included in the cluster.

The individual load feature calculation unit 204 receives the posture load information from the posture load calculation unit 202, and receives the first clustering result from the first clustering unit 203. The individual load feature calculation unit 204 calculates an individual load feature based on the posture load information and the first clustering result. The individual load feature calculation unit 204 outputs information on the calculated individual load feature (individual load feature information) to the second clustering unit 205.

The individual load feature information is, for example, data in which a sample and a distance between the sample and each of a plurality of representative samples are associated with each other for each of a plurality of samples. For example, the individual load feature calculation unit 204 calculates an absolute value of a difference in posture load between two samples as a distance. As the distance between the two samples is closer to zero, it can be seen that the two samples have similar posture loads.

The second clustering unit 205 receives the individual load feature information from the individual load feature calculation unit 204. The second clustering unit 205 performs second clustering using the individual load feature information, and generates a second clustering result. The second clustering unit 205 outputs the generated second clustering result to the total load feature calculation unit 206.

The second clustering result includes, for example, data in which a sample ID and a cluster ID (second cluster ID) for distinguishing each cluster in the second clustering are associated with each other. Note that the second clustering result may include information on the representative sample in each cluster.

The total load feature calculation unit 206 receives the second clustering result from the second clustering unit 205. The total load feature calculation unit 206 calculates a total load feature based on the second clustering result. The total load feature calculation unit 206 outputs information on the calculated total load feature (total load feature information) to the display control unit 207. Note that the total load feature calculation unit 206 may determine the load attribute for the second cluster ID. The load attribute is information on the type of load of the cluster. Hereinafter, it is assumed that some attributes are assigned to each cluster classified by the second clustering.

The total load feature information includes, for example, data on load strength (load strength data) for determining the attribute of the cluster and data (load attribute data) relating to the load attribute indicating the attribute of the load for the worker. The load strength data is, for example, a graph (load strength graph) of an average value for each posture load of samples included in a cluster, for each cluster (alternatively, for each attribute). The load attribute data is, for example, a graph (load attribute graph) obtained by plotting samples in time series for each cluster (alternatively, for each attribute). The total load feature information may include data in which the second cluster ID and the load attribute are associated with each other.

The display control unit 207 receives the total load feature information from the total load feature calculation unit 206. The display control unit 207 generates display data based on the total load feature information, and displays the display data on a display that is the output apparatus 110. Alternatively, the display control unit 207 displays display data including a posture load graph illustrating posture loads in time series on the display.

The configurations of the load estimation system 1 and the load estimation apparatus 100 according to the first embodiment have been described above. Next, the operation of the load estimation apparatus 100 will be described with reference to the flowchart of FIG. 3.

Figure 3:
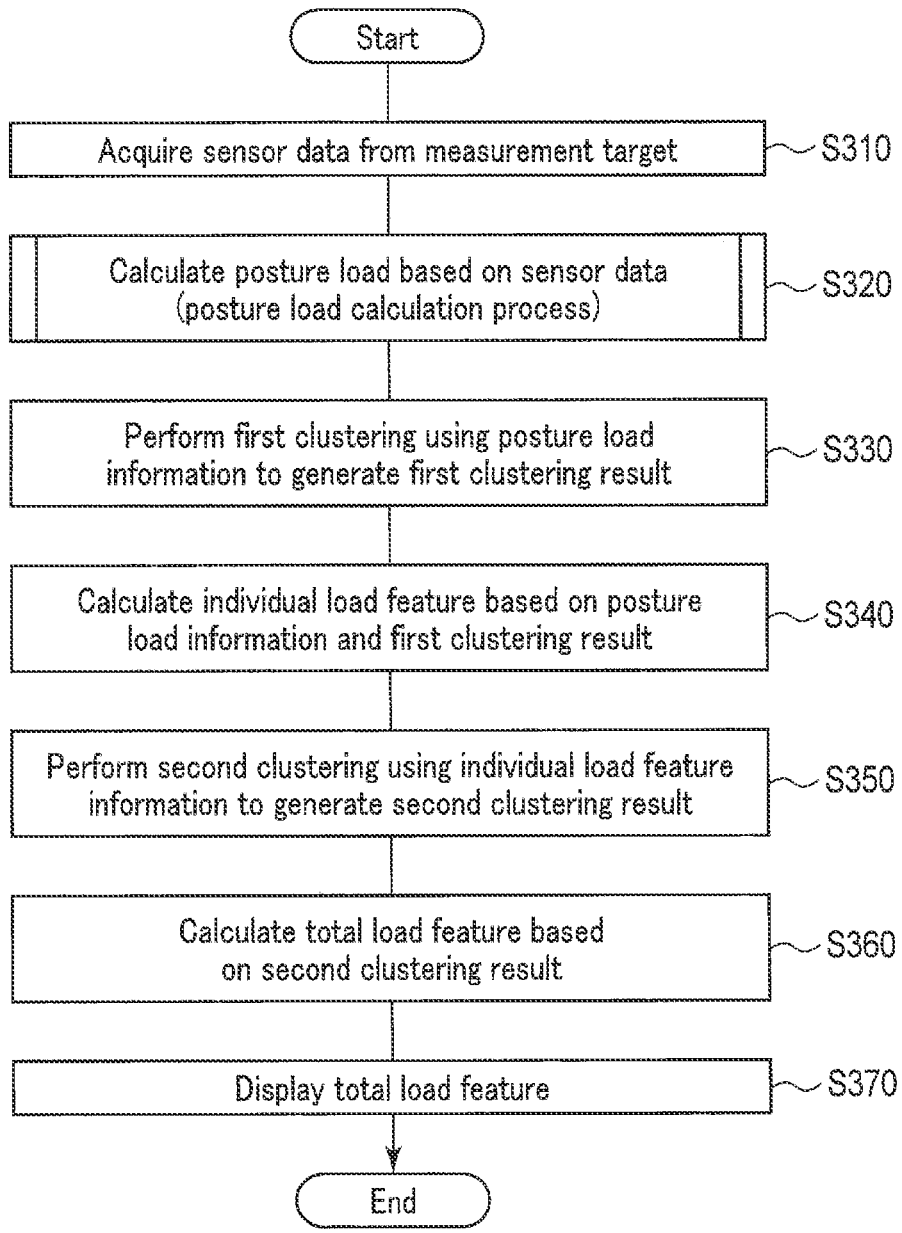
FIG. 3 is a flowchart illustrating an operation of the load estimation apparatus according to the first embodiment.

FIG. 3 is a flowchart illustrating the operation of the load estimation apparatus according to the first embodiment. The process of the flowchart of FIG. 3 starts when a load estimation program is executed by the user.

(Step S310)

When the load estimation program is executed, the data acquisition unit 201 acquires sensor data from the measurement target.

(Step S320)

After the sensor data is acquired, the posture load calculation unit 202 calculates a posture load based on the sensor data. Hereinafter, the process in Step S320 is referred to as a "posture load calculation process". A specific example of the posture load calculation process will be described with reference to the flowchart of FIG. 4.

Figure 4:
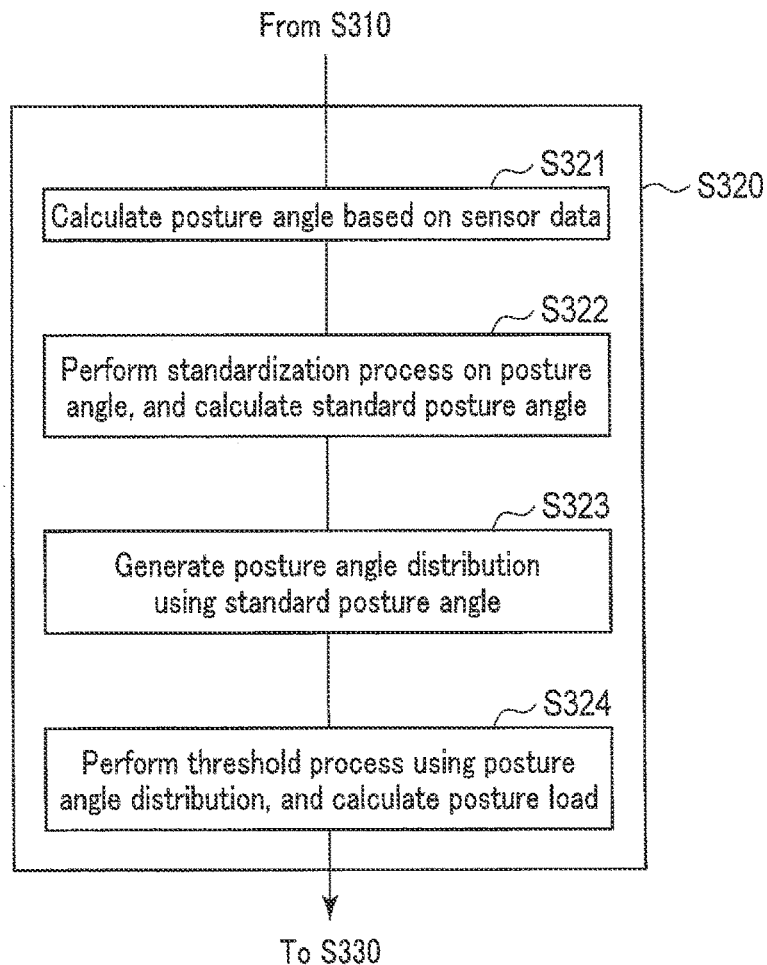
FIG. 4 is a flowchart illustrating a posture load calculation process of the flowchart of FIG. 3.

FIG. 4 is a flowchart illustrating the posture load calculation process of the flowchart of FIG. 3. The flowchart of FIG. 4 proceeds from Step S320.

(Step S321)

After the sensor data is acquired, the posture load calculation unit 202 calculates a posture angle based on the sensor data. Specifically, the posture load calculation unit 202 calculates an angle between the sensor reference axis and the gravity direction from a pattern of the sensor data, and sets the angle as the posture of the sensor attachment part.

Figure 5:
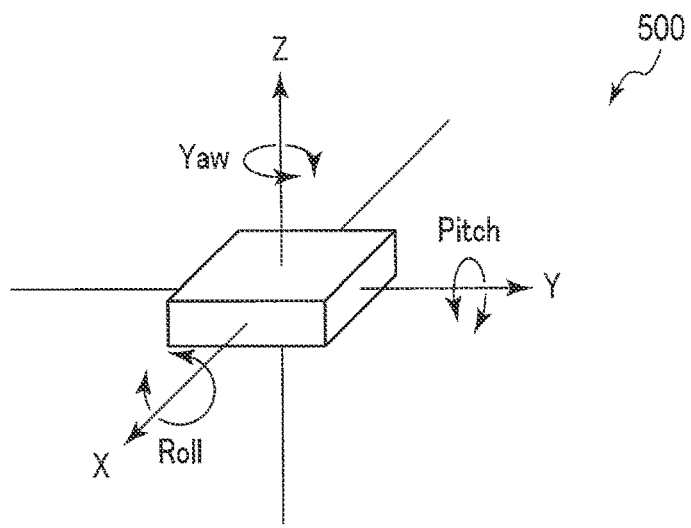
FIG. 5 is a diagram for describing a relationship among a sensor, a sensor reference axis, and a rotation angle in the first embodiment.

FIG. 5 is a diagram for describing a relationship among the sensor, the sensor reference axis, and the rotation angle in the first embodiment. A sensor 500 of FIG. 5 is, for example, an acceleration sensor. The sensor 500 acquires sensor data corresponding to three orthogonal sensor reference axes (X axis, Y axis, Z axis). At this time, the rotation angle around the X axis is referred to as a roll angle, the rotation angle around the Y axis is referred to as a pitch angle, and the rotation angle around the Z axis is referred to as a yaw angle.

Figure 6:
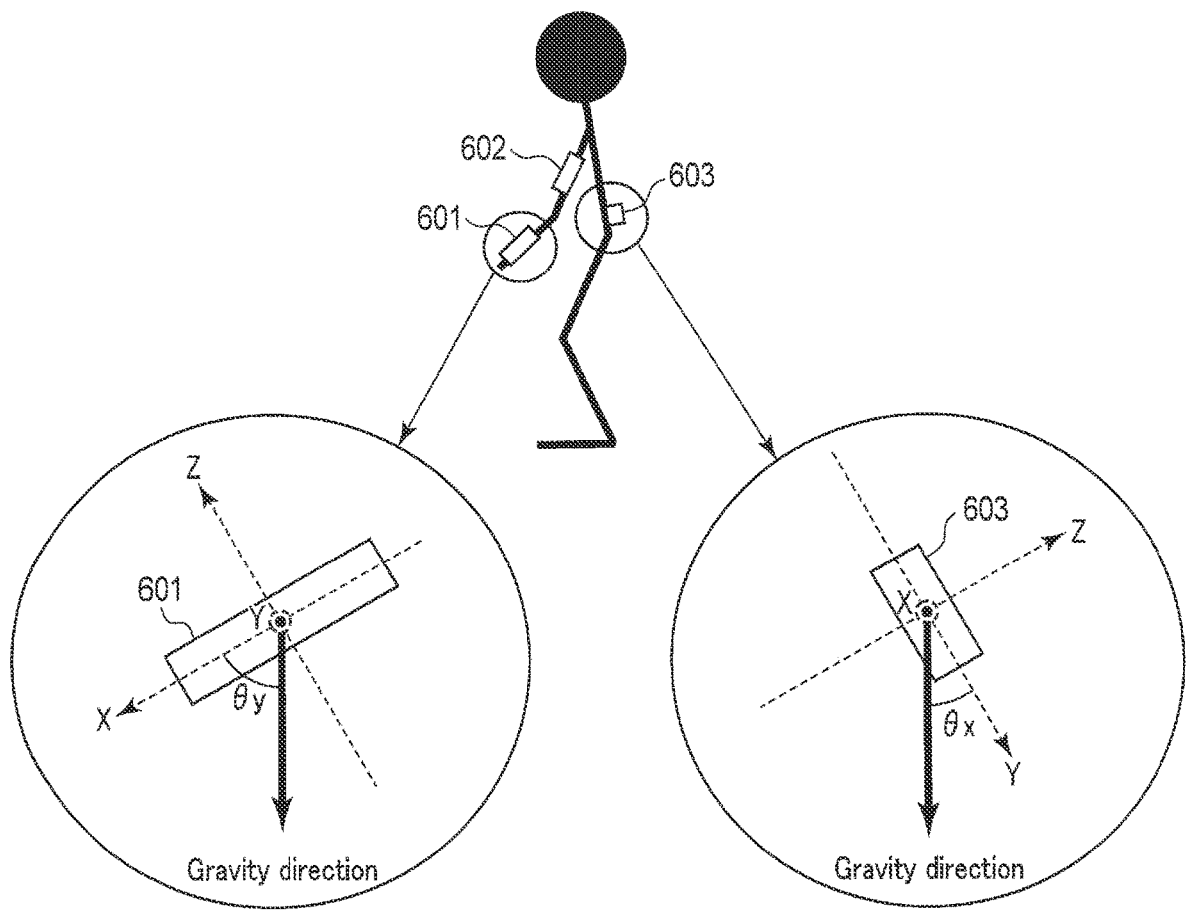
FIG. 6 is a diagram for describing a sensor attachment part and a sensor attachment direction in the first embodiment.

FIG. 6 is a diagram for describing the sensor attachment part and the sensor attachment direction in the first embodiment. FIG. 6 illustrates a state in which a first sensor 601, a second sensor 602, and a third sensor 603 are worn on the wrist, the upper arm, and the waist of the user, respectively.

For example, the first sensor 601 is attached such that the X axis corresponds to the extending direction of the wrist (that is, a direction from the elbow to the fingertip). The posture load calculation unit 202 calculates an angle θy between the X axis as a reference and the gravity direction from the pattern of the sensor data of the first sensor 601. The calculated angle θy corresponds to the pitch angle of the first sensor 601. Then, the posture load calculation unit 202 calculates the posture angle of the wrist based on the calculated angle θy and an offset angle.

The offset angle is determined with a stationary state of the attachment part as a reference. For example, in a case where the posture angle of the wrist is calculated, when a state in which the positive direction of the X axis and the gravity direction are matched is set as the stationary state, the offset angle is 0 degrees, and when a state in which the X axis and the gravity direction are orthogonal to each other is set as the stationary state, the offset angle is 90 degrees. Hereinafter, a case where the offset angle is zero degrees will be described.

For example, the second sensor 602 is attached such that the X axis corresponds to the extending direction of the upper arm (that is, a direction from the shoulder to the elbow). The posture load calculation unit 202 calculates a posture angle of the upper arm based on the sensor data of the second sensor 602. Since a specific calculation method and the like are similar to those in the case of the first sensor 601, the description thereof will be omitted.

For example, the third sensor 603 is attached such that the X axis corresponds to a direction around the waist. In other words, for example, the third sensor 603 is attached such that the Y axis corresponds to the extending direction of the backbone. The posture load calculation unit 202 calculates an angle θx between the Y axis as a reference and the gravity direction from the pattern of the sensor data of the third sensor 603. The calculated angle θx corresponds to the roll angle of the third sensor 603. Then, the posture load calculation unit 202 calculates the posture angle of the waist based on the calculated angle θx and the offset angle. In a case where the posture angle of the waist is calculated, when a state in which the positive direction of the Y axis and the gravity direction are matched is set as the stationary state, the offset angle is 0 degrees.

When summarizing the sensor in the embodiment, the stationary state of the sensor is a state (upright state) in which the worker vertically lowers the arm with respect to the ground and stands upright. Therefore, since the posture change of the worker from the upright state can be detected, the posture load calculation unit 202 can calculate the posture of the worker as the angle of each body part.

(Step S322)

After the posture angle is calculated, the posture load calculation unit 202 performs the standardization process on the posture angle, and calculates the standard posture angle. Specifically, the posture load calculation unit 202 performs the standardization process on a plurality of posture angles calculated for each acquired sample over an acquisition period of sensor data, for each part of the attachment parts. The standardization process is, for example, a data scaling process and a shift process in which the average is set to zero and the variance is set to one. The standardization process is performed so that a standard work posture for each worker can be considered.

(Step S323)

After the standard posture angle is calculated, the posture load calculation unit 202 generates a posture angle distribution using the standard posture angle. Specifically, the posture load calculation unit 202 generates the posture angle distribution in which the relationship between the posture angle and the gravity direction is illustrated in a graph.

Figure 7:
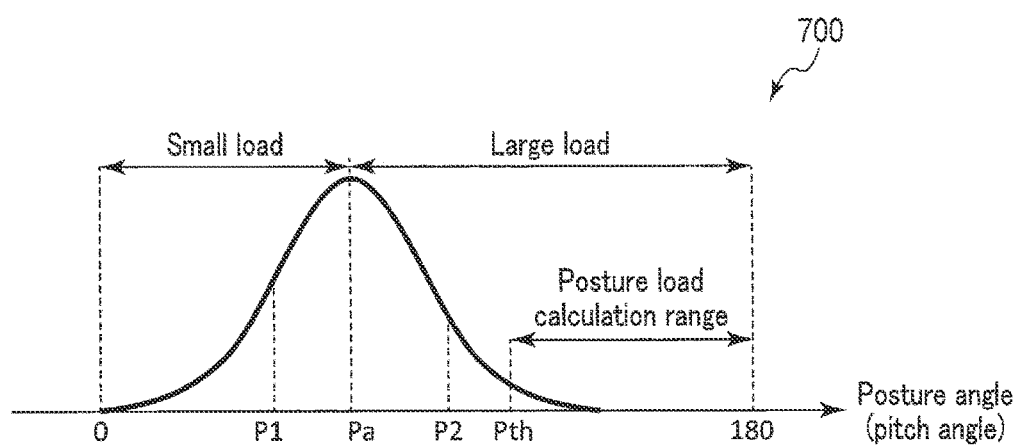
FIG. 7 is a graph illustrating a distribution obtained by standardizing a posture angle of the sensor attached to an upper arm in the first embodiment.

FIG. 7 is a graph illustrating a distribution obtained by standardizing the posture angle of the sensor attached to the upper arm in the first embodiment. A graph 700 of FIG. 7 illustrates a distribution of the posture angles centered on an average posture angle Pa. The average posture angle Pa indicates an average of the calculated posture angles. In the graph 700, a posture angle (for example, a posture angle P1 of the graph 700) smaller than the average posture angle Pa has a small physical load, and a posture angle (for example, a posture angle P2 of the graph 700) larger than the average posture angle Pa has a large physical load.

Figure 8:
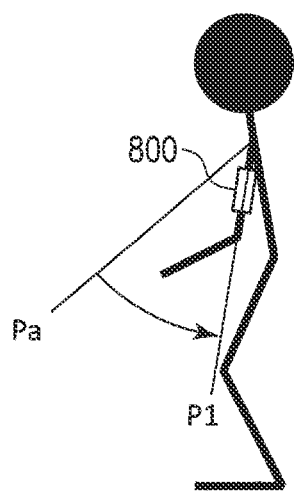
FIG. 8 is a diagram for describing a posture of the upper arm in a case where the load is small in the graph of FIG. 7.

FIG. 8 is a diagram for describing the posture of the upper arm in a case where the load is small in the graph 700 of FIG. 7. In FIG. 8, the sensor data output from a sensor 800 indicates the posture angle P1 smaller than the average posture angle Pa of the upper arm. Since the upper arm of the worker is lower than the average posture angle Pa, the load of the worker becomes small.

Figure 9:
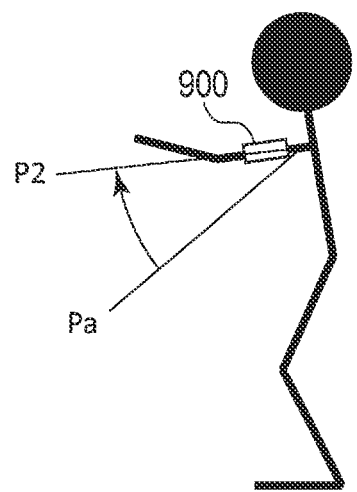
FIG. 9 is a diagram for describing a posture of the upper arm in a case where the load is large in the graph of FIG. 7.

FIG. 9 is a diagram for describing the posture of the upper arm in a case where the load is large in the graph 700 of FIG. 7. In FIG. 9, the sensor data output from a sensor 900 indicates the posture angle P2 larger than the average posture angle Pa of the upper arm. Since the upper arm of the worker is higher than the average posture angle Pa, the load of the worker becomes large.

(Step S324)

After the posture angle distribution is generated, the posture load calculation unit 202 performs the threshold process using the posture angle distribution, and calculates the posture load. Specifically, the posture load calculation unit 202 performs the threshold process on each posture angle distribution for each part, and calculates the posture load. After Step S324, the process proceeds to Step S330 of FIG. 3.

For example, in the graph 700 of FIG. 7, it is assumed that the posture load is calculated for a posture angle larger than a posture angle Pth with the posture angle Pth as a threshold. The posture load calculation unit 202 calculates a value of a difference between the measured posture angle and the posture angle Pth, as the posture load. The posture angle Pth serving as the threshold is determined based on the posture angle distribution. Note that the posture angle Pth may be arbitrarily set, and may be, for example, a value larger than the average posture angle Pa.

Although the upper arm has been described above, the posture load calculation unit 202 similarly generates posture angle distributions for the wrist and the waist, performs the threshold process for each of the wrists and the waist, and calculates the posture load. For example, when the posture angle distribution of the upper arm and the posture angle distribution of the wrist are compared, the posture angle distribution of the wrist often indicates a larger value as a whole. Thus, the posture load calculation unit 202 can improve the accuracy of the calculated posture load by setting different thresholds for respective parts and performing the threshold process for each of the parts.

Figure 10:
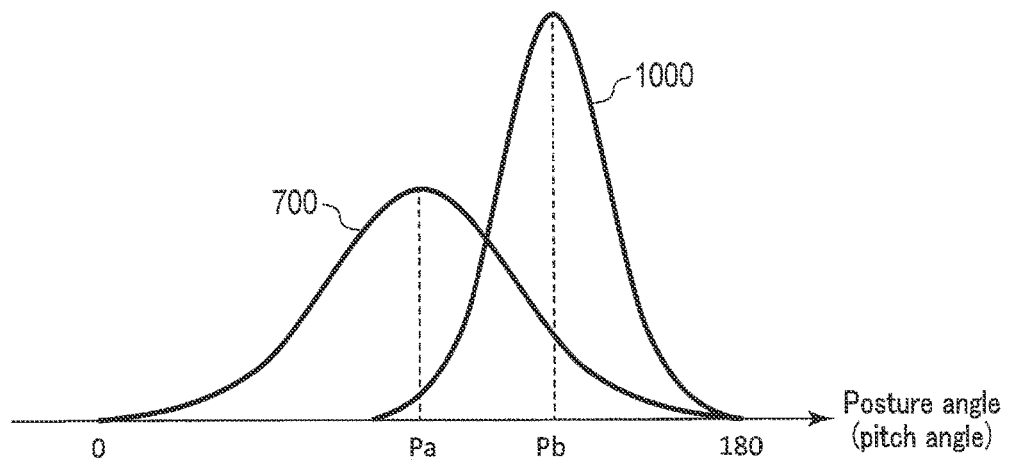
FIG. 10 is a diagram for describing a relationship between a graph that illustrates a distribution obtained by standardizing a posture angle of the sensor attached to the upper arm, and a graph that illustrates a distribution obtained by standardizing a posture angle of the sensor attached to a wrist in the first embodiment.

FIG. 10 is a diagram for describing a relationship between a graph that illustrates a distribution obtained by standardizing the posture angle of the sensor attached to the upper arm, and a graph that illustrates a distribution obtained by standardizing the posture angle of the sensor attached to the wrist in the first embodiment. A graph 1000 of FIG. 10 illustrates a distribution of the posture angle centered on an average posture angle Pb, of the wrist. The average posture angle Pb is larger than the average posture angle Pa in the graph 700. As a result, it can be seen that the average posture angle based on the magnitude of the load is different for each part.

Figure 11:
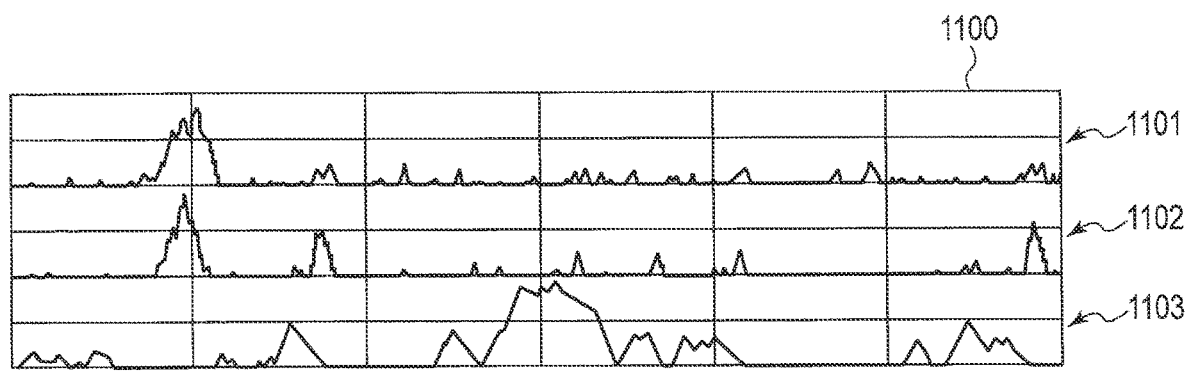
FIG. 11 is a graph illustrating three-dimensional posture load information in time series in the first embodiment.

FIG. 11 is a graph illustrating three-dimensional posture load information in time series in the first embodiment. A posture load graph 1100 of FIG. 11 includes a graph 1101 of the posture load relating to the wrist, a graph 1102 of the posture load relating to the upper arm, and a graph 1103 of the posture load relating to the waist. In each graph, the horizontal axis represents time, and the vertical axis represents the load strength. In the posture load graph 1100, the larger the value on the vertical axis, the higher the load strength.

(Step S330)

After the posture load information is calculated, the first clustering unit 203 performs the first clustering using the posture load information, and generates the first clustering result. Specifically, the first clustering unit 203 classifies the three-dimensional sample data included in the posture load information into an arbitrary number of clusters by performing a clustering process. Then, the first clustering unit 203 determines a representative sample by aggregating and averaging the samples included in the cluster for each of the classified clusters.

In the first clustering, the number of clusters to be classified is desirably higher than the number of dimensions of the sample data, and is, for example, four or more. This is to make the number of dimensions of the individual load feature described later higher than the number of dimensions of the posture load information so as not to depend on the sensor attachment part. In addition, the number of clusters to be classified is determined by the user. The first clustering result is, for example, three-dimensional coordinates of the representative sample determined in each cluster.

Hereinafter, as the first clustering, a specific example of classifying three-dimensional sample data of the posture load information into seven clusters will be described with reference to FIGS. 12 to 14.

Figure 12:
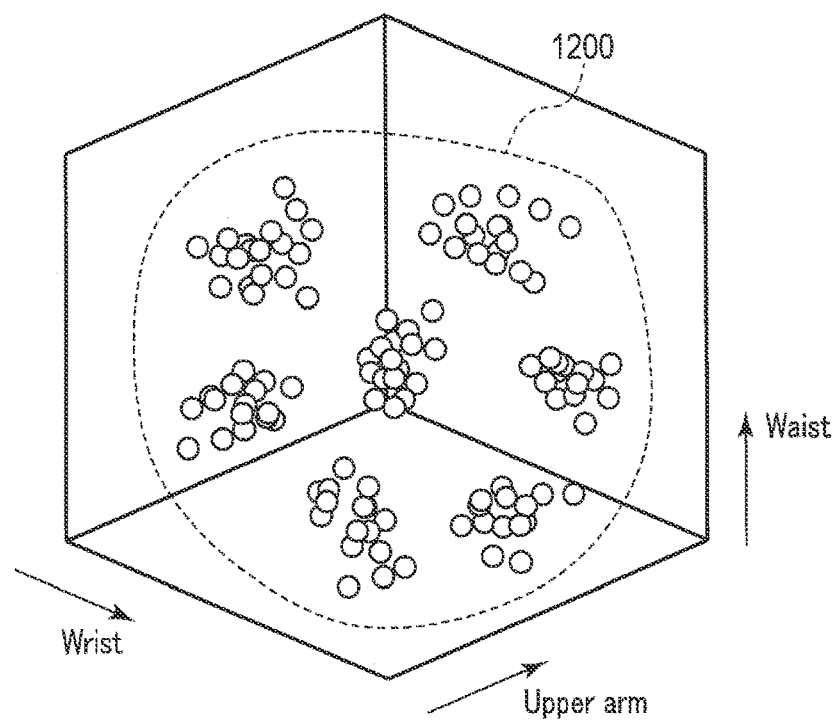
FIG. 12 is a diagram for describing a plot of posture load information on three-dimensional coordinates in the first embodiment.

FIG. 12 is a diagram for describing a plot of the posture load information on three-dimensional coordinates in the first embodiment. In FIG. 12, the posture load of the wrist, the posture load of the upper arm, and the posture load of the waist are respectively associated with three axes in three-dimensional coordinates. A sample set 1200 of FIG. 12 represents a set of a plurality of samples of the posture load information.

Figure 13:
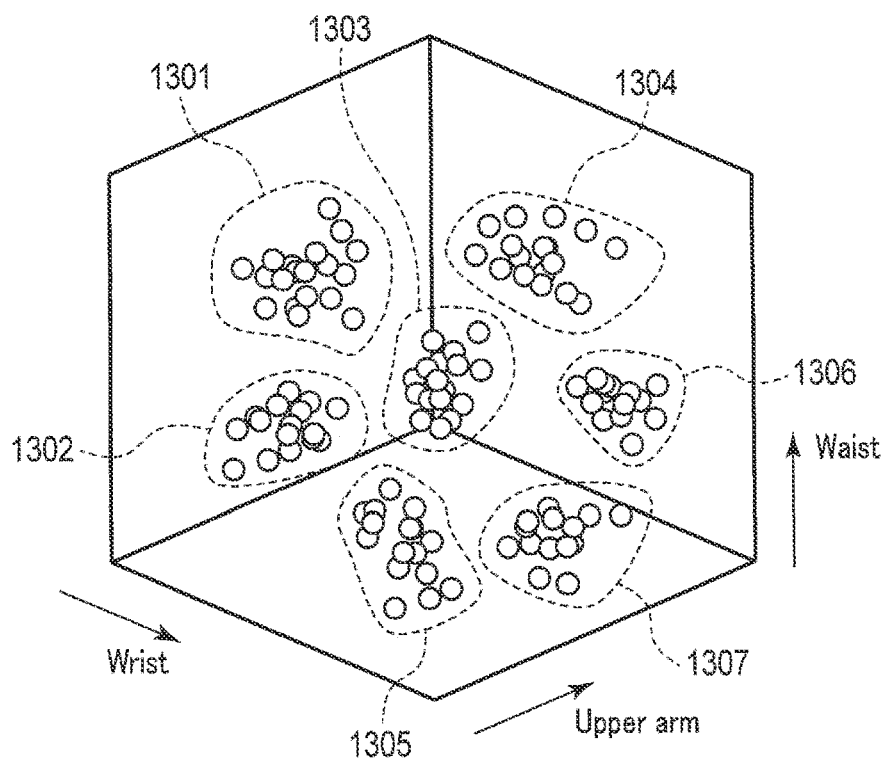
FIG. 13 is a diagram for describing a clustering result of FIG. 12.

FIG. 13 is a diagram for describing a clustering result of FIG. 12. In FIG. 13, a first cluster 1301, a second cluster 1302, a third cluster 1303, a fourth cluster 1304, a fifth cluster 1305, a sixth cluster 1306, and a seventh cluster 1307 are illustrated as the seven clusters. The first clustering unit 203 classifies the sample set 1200 into the above-described seven clusters.

Figure 14:
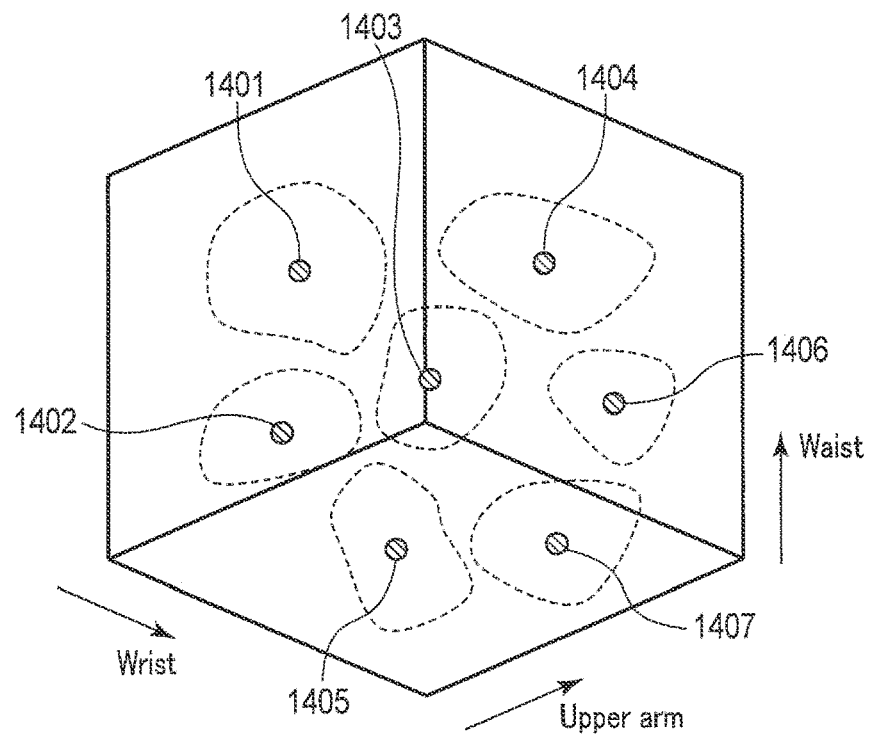
FIG. 14 is a diagram for describing a representative sample in each cluster of FIG. 13.

FIG. 14 is a diagram for describing a representative sample in each cluster of FIG. 13. FIG. 14 illustrates a first representative sample 1401, a second representative sample 1402, a third representative sample 1403, a fourth representative sample 1404, a fifth representative sample 1405, a sixth representative sample 1406, and a seventh representative sample 1407 as representative samples of the seven clusters. The first clustering unit 203 determines the above-described seven representative samples by aggregating and averaging the samples included in the cluster for each of the classified seven clusters.

(Step S340)

After the first clustering result is generated, the individual load feature calculation unit 204 generates an individual load feature based on the posture load information and the first clustering result. Specifically, the individual load feature calculation unit 204 calculates the distance to each of the plurality of representative samples for all the acquired samples (for example, sample set 1200 of FIG. 12). Then, the individual load feature calculation unit 204 generates, for each of all the samples, an individual load feature having a plurality of elements in which the distance between the sample and the representative sample is one element.

Figure 15:
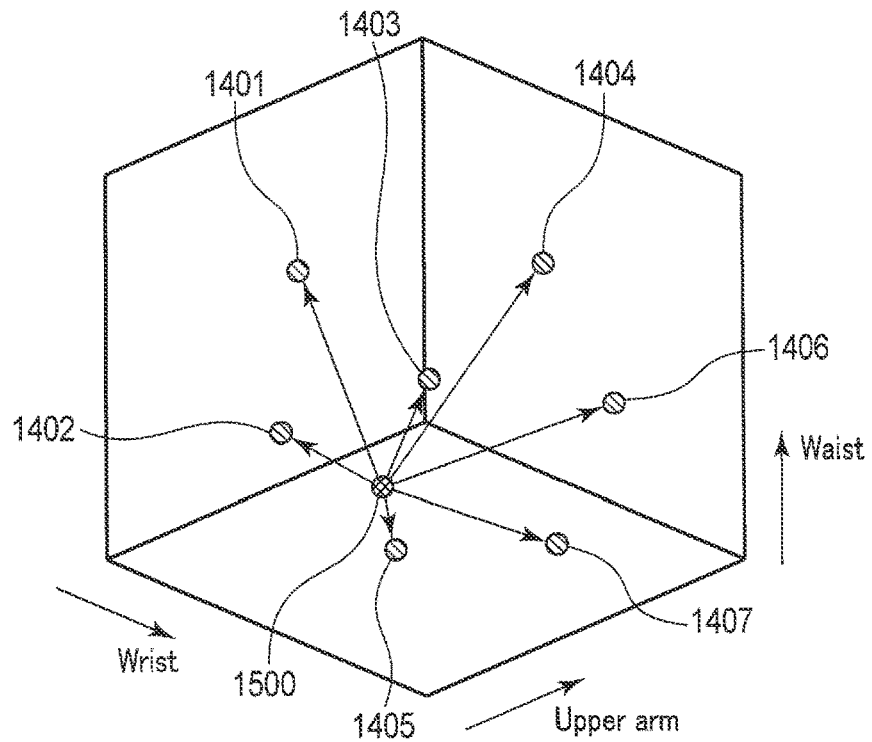
FIG. 15 is a diagram for describing distances from a specific sample to a plurality of representative samples.

FIG. 15 is a diagram for describing distances from a specific sample to a plurality of representative samples. In FIG. 15, distances from a specific sample 1500 of the sample set 1200 to a plurality of representative samples are indicated by arrows. The individual load feature calculation unit 204 calculates a distance using, for example, the absolute value of the difference between the coordinates of the sample 1500 and the coordinates of the first representative sample 1401. Similarly, by calculating the distances to other representative samples, the individual load feature calculation unit 204 generates seven-dimensional distance data having seven distances as elements, for the sample 1500.

(Step S350)

After the individual load feature is generated, the second clustering unit 205 performs the second clustering using the individual load feature information, and generates the second clustering result. Specifically, the second clustering unit 205 classifies the seven-dimensional distance data included in the individual load feature information into an arbitrary number of clusters by performing the clustering process. In the second clustering, the number of clusters to be classified is desirably equal to or lower than the number of dimensions of the distance data. That is, the second clustering is classified into a number of clusters equal to or lower than the number of clusters in the first clustering. In addition, the number of clusters to be classified is determined by the user.

(Step S360)

After the second clustering result is generated, the total load feature calculation unit 206 generates the total load feature based on the second clustering result. Specifically, the total load feature calculation unit 206 generates the load strength graph and the load attribute graph by aggregating and averaging the samples included in the cluster, for each of the classified clusters.

Figure 16:
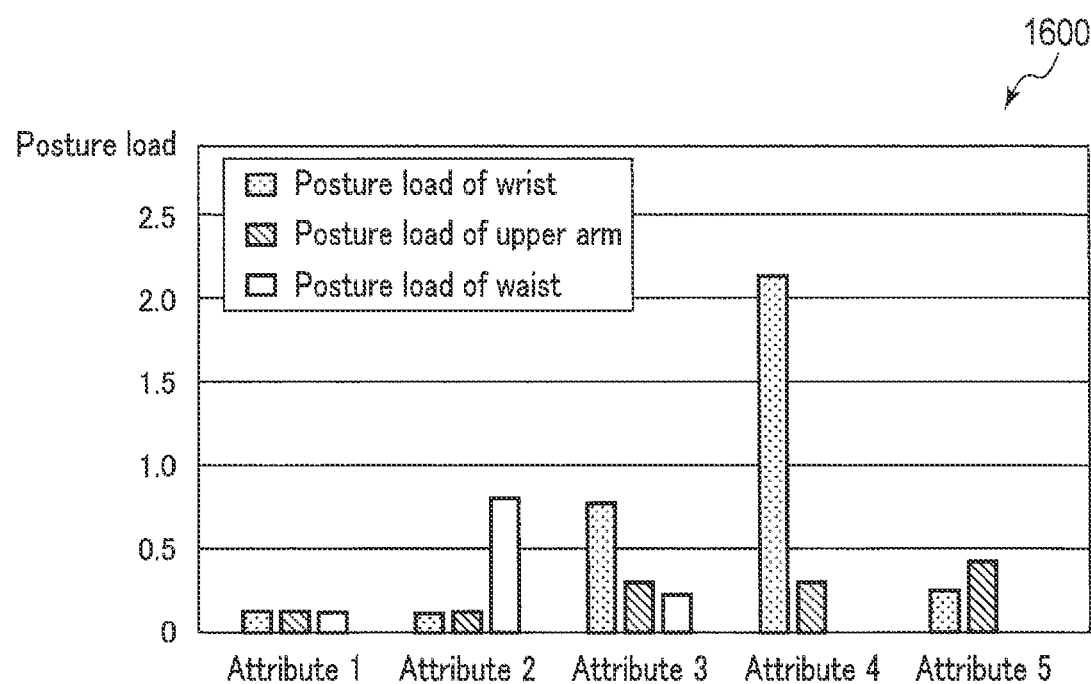
FIG. 16 is a diagram illustrating a load strength graph of a total load feature in the first embodiment.

FIG. 16 is a diagram illustrating the load strength graph of the total load feature in the first embodiment. A load strength graph 1600 of FIG. 16 illustrates, for each cluster (attribute), an average value of each posture load of all the samples included in the cluster. For example, in an attribute 1, the posture load of the wrist, the posture load of the upper arm, and the posture load of the waist are equal to each other.

In the attribute 2 and the attribute 3, the posture load of the waist and the posture load of the wrist are higher than the posture loads of the other parts, respectively. In addition, in the attribute 4, the posture load of the wrist is the highest among the parts including other attributes.

The total load feature calculation unit 206 may determine each attribute name for each attribute of the load strength graph 1600. For example, in the case of the attribute 1, since all the posture loads of the respective parts are substantially equal, the total load feature calculation unit 206 determines the attribute name of an "average load type" for the cluster of the attribute 1. Further, in the case of the attribute 4, since the posture load of the wrist is higher than the posture loads of the other parts, the total load feature calculation unit 206 determines the attribute name of a "wrist load type" for the cluster of the attribute 4. The attribute name may be determined not only with respect to the feature of each part but also with respect to the total load obtained by summing the loads of the parts. For example, the total load feature calculation unit 206 may determine the attribute name of a "high-load type" in a case where the total load is high, and may determine the attribute name of a "low-load type" in a case where the total load is low.

Figure 17:
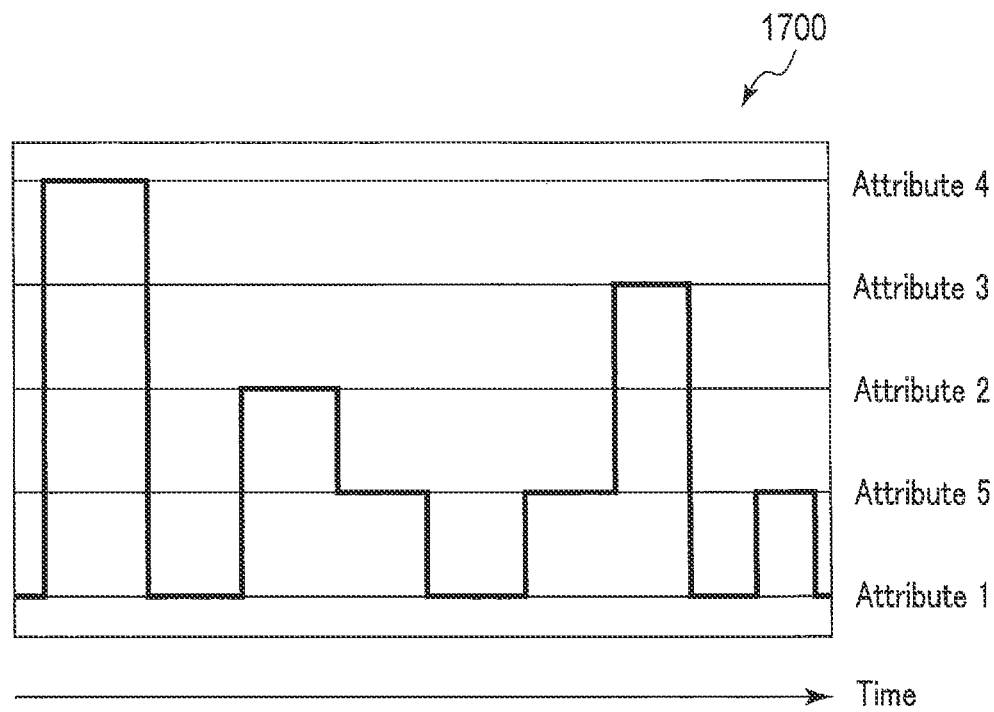
FIG. 17 is a diagram illustrating a load attribute graph of a total load feature in the first embodiment.

FIG. 17 is a diagram illustrating a load attribute graph of a total load feature in the first embodiment. In a load attribute graph 1700 of FIG. 17, a graph in which samples are plotted in time series for each attribute is illustrated. Attributes are set on the vertical axis of the graph, and are sorted based on the sum of the posture loads of each attribute. The sum of the posture loads is the sum of the posture load of the wrist, the posture load of the upper arm, and the posture load of the waist. In the load attribute graph 1700, the attribute 4 of which the sum of the posture loads is the largest is set at the top of the vertical axis. As a result, attributes with a high load gather on the upper side in the graph, so that the user can efficiently search for a work section with a high load that requires improvement. In addition, since the samples are plotted for each attribute, for example, in a case where an attribute name is attached to the attribute, it is possible to efficiently search for a work section that requires improvement by focusing on the feature of the load.

(Step S370)

After the total load feature is generated, the display control unit 207 displays the display data based on the total load feature information. Specifically, the display control unit 207 causes the display that is the output apparatus 110 to display the display data. After the process of Step S370, the load estimation program is ended.

As described above, the load estimation apparatus according to the first embodiment acquires sensor data from a measurement target, calculates one or more posture loads relating to one or more body parts of the measurement target based on the sensor data, and displays display data including a posture load graph in which the one or more posture loads are illustrated in time series. Furthermore, the load estimation apparatus may calculate the posture load based on the distribution of the posture angles of the body part.

Therefore, the load estimation apparatus according to the first embodiment can perform load estimation in consideration of the motion of the worker by calculating the posture load for each body part and displaying the calculated posture load in time series.

Alternatively, the load estimation apparatus according to the first embodiment acquires sensor data from a measurement target, calculates one or more posture loads relating to one or more body parts of the measurement target based on the sensor data, performs first clustering of classifying the posture loads into a number of dimensions higher than the number of dimensions of the information on the posture loads using the information on the posture loads to generate a first clustering result, performs second clustering of classifying the posture loads into a number of dimensions equal to or less than the number of dimensions of the first clustering based on the information on the posture loads and the first clustering result to generate a second clustering result, and calculates a total load feature relating to the measurement target based on the second clustering result.

Therefore, since the load estimation apparatus according to the first embodiment can calculate the load feature independent of the body part, it is possible to perform the load estimation in consideration of the motion of the worker.

Therefore, by using the load estimation apparatus according to the first embodiment, it is possible to optimize the operation at the work site, such as reviewing the work process in manufacturing and distribution, assigning the work to the worker, and appropriately setting the break time.

Second Embodiment

In the first embodiment, the load estimation relating to a specific worker has been described. On the other hand, in the second embodiment, a description will be given of selecting a worker from a plurality of workers and performing load estimation for the selected worker.

Figure 18:
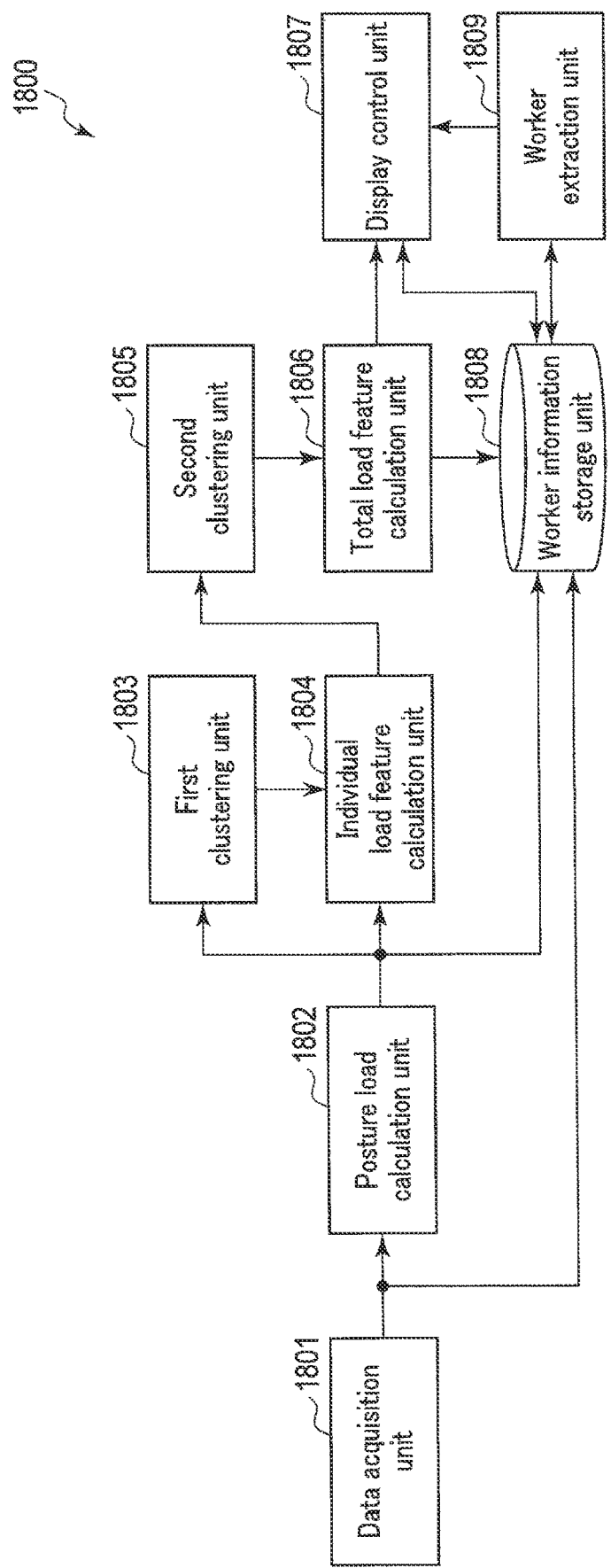
FIG. 18 is a block diagram illustrating a configuration of a load estimation apparatus according to a second embodiment.

FIG. 18 is a block diagram illustrating a configuration of a load estimation apparatus according to a second embodiment. A load estimation apparatus 1800 of FIG. 18 includes a data acquisition unit 1801, a posture load calculation unit 1802, a first clustering unit 1803 (first generation unit), an individual load feature calculation unit 1804, a second clustering unit 1805 (second generation unit), a total load feature calculation unit 1806, a display control unit 1807, a worker information storage unit 1808 (measurement target information storage unit), and a worker extraction unit 1809 (measurement target extraction unit).

Note that the data acquisition unit 1801, the posture load calculation unit 1802, the first clustering unit 1803, the individual load feature calculation unit 1804, the second clustering unit 1805, and the total load feature calculation unit 1806 have the same configurations as the data acquisition unit 201, the posture load calculation unit 202, the first clustering unit 203, the individual load feature calculation unit 204, the second clustering unit 205, and the total load feature calculation unit 206 in FIG. 2, and thus, description thereof is omitted.

The worker information storage unit 1808 receives sensor data from the data acquisition unit 1801, receives posture load information from the posture load calculation unit 1802, and receives total load feature information from the total load feature calculation unit 1806. The worker information storage unit 1808 stores sensor data, posture load information, and total load feature information in association with each other. The worker information storage unit 1808 stores these pieces of information for each of the plurality of measurement targets.

Specifically, the worker information storage unit 1808 stores, for example, a worker information table in which time, the name of the worker (worker ID), posture load information, and sensor data are associated with each other. The worker information storage unit 1808 outputs the worker information table to the display control unit 1807 and the worker extraction unit 1809. The information in which the posture load information and the sensor data are associated with each other may be referred to as work information.

The worker extraction unit 1809 accepts the selection of the worker from the user, and reads the worker information table from the worker information storage unit 1808. Then, the worker extraction unit 1809 extracts the work information of the selected worker from the worker information table. The worker extraction unit 1809 outputs the extracted work information to the display control unit 1807.

The display control unit 1807 receives the work information extracted from the worker extraction unit 1809. The display control unit 1807 displays display data based on the extracted work information.

Figure 19:
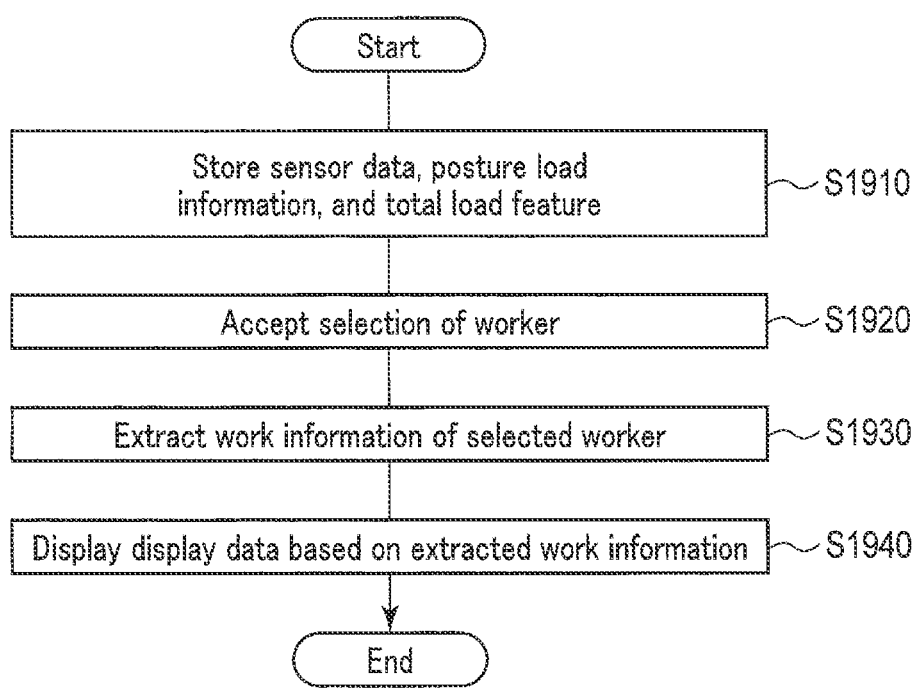
FIG. 19 is a flowchart illustrating an operation of the load estimation apparatus according to the second embodiment.

FIG. 19 is a flowchart illustrating an operation of the load estimation apparatus according to the second embodiment. The process of the flowchart of FIG. 19 is started, for example, after the process of the flowchart of FIG. 3 (after the process of Step S370) when the load estimation program is executed by the user.
(Step S1910)

After the process of Step S370, the worker information storage unit 1808 stores sensor data, posture load information, and total load feature information in association with each other. Specifically, the worker information storage unit 1808 stores various kinds of information in the worker information table while the total load feature information is being generated. A specific example of the worker information table will be described with reference to FIG. 20.

FIG. 20 is a table in which time, a worker ID, posture load information, and sensor data are associated with each other in the second embodiment. In a table 2000 (worker information table) of FIG. 20, time, a worker ID, posture load information (the load value of the upper arm, the load value of the wrist, and the load value of the waist), and sensor data (acceleration on the X axis, acceleration on the Y axis, and acceleration on the Z axis) are associated with each other. Note that, in the table 2000, sensor data acquired from one sensor is associated as an example, but data from all the sensors may be associated. In the worker information table, the load attribute may further be associated.
(Step S1920)

After the storage process in the worker information storage unit 1808 is ended, the load estimation apparatus 100 accepts the selection of the worker from the user. At this time, the user can select a worker from a pull-down menu displayed in display data to be described later.
(Step S1930)

After the worker is selected, the worker extraction unit 1809 reads the worker information table from the worker information storage unit 1808, and extracts the work information of the selected worker.
(Step S1940)

After the work information is extracted, the display control unit 1807 displays display data based on the extracted work information. After the process of Step S1940, the process of the flowchart of FIG. 19 is ended.

Figure 21:
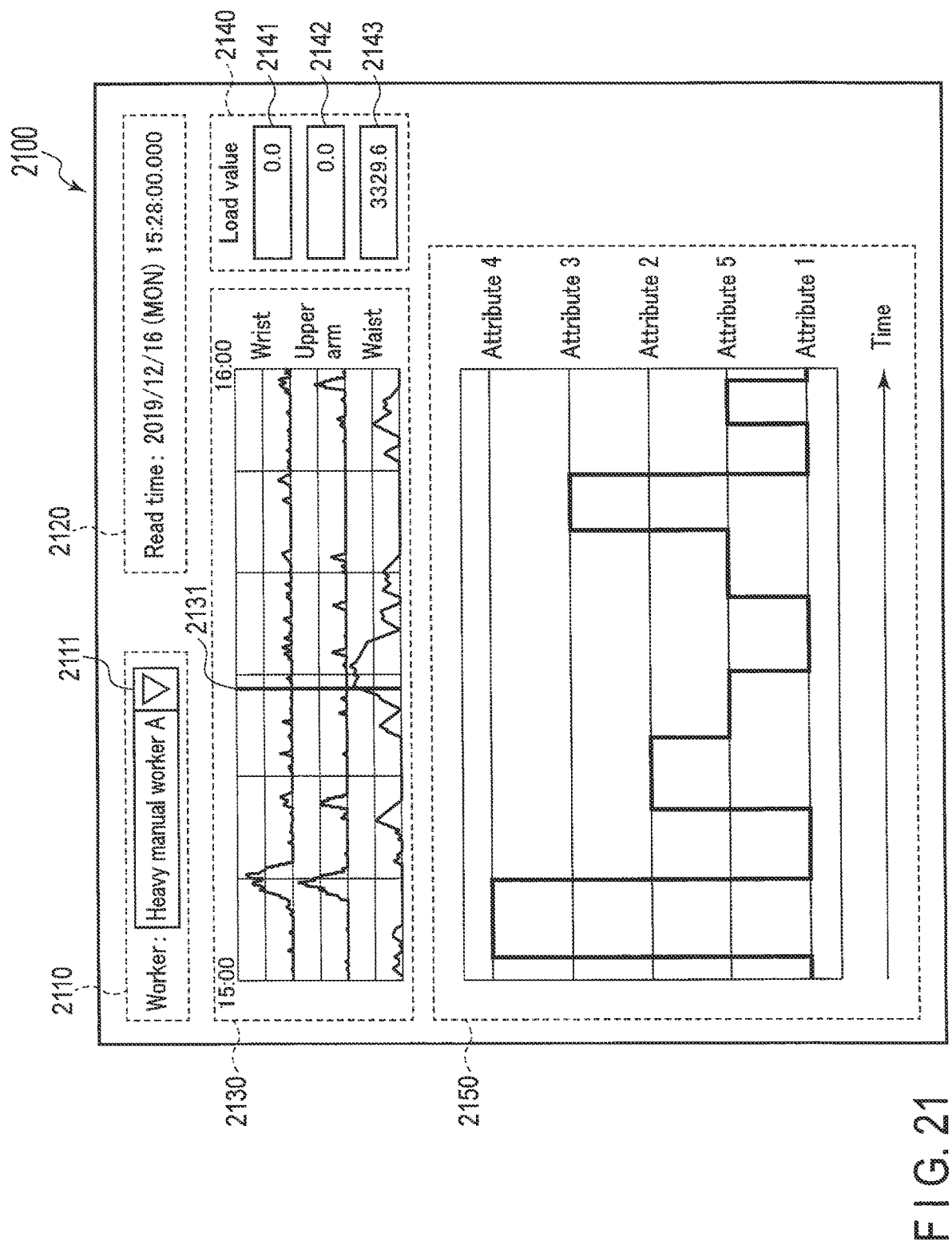
FIG. 21 is an example of display data in the second embodiment.

FIG. 21 is an example of display data in the second embodiment. Display data 2100 of FIG. 21 includes, for example, a display area 2110 for the worker name, a display area 2120 for the read time, a display area 2130 for the posture load graph, a display area 2140 for the load value, and a display area 2150 for the load attribute graph.

In the display area 2110, a pull-down menu 2111 in which the names of the workers are displayed and stored is displayed. In the display area 2120, the read time of the acquired work information is displayed. In the display area 2130, the posture load graph is displayed. A slider 2131 indicating the position of the read time is superimposed on the posture load graph. In the display area 2140, the posture load value at the read time is displayed. The load attribute graph is displayed in the display area 2150.

In a case where the user selects a worker ID "heavy manual worker A" from the pull-down menu 2111, for example, the display control unit 1807 displays information corresponding to the selected worker ID in the display area 2120, the display area 2130, the display area 2140, and the display area 2150.

Note that the display data is not limited to the display of the above information and graph. For example, the load strength graph 1600 of FIG. 16 may be further displayed in the display data. For example, the load attribute graph may not be displayed in the display data.

As described above, the load estimation apparatus according to the second embodiment acquires sensor data from a measurement target, calculates one or more posture loads relating to one or more body parts of the measurement target based on the sensor data, and displays display data including a posture load graph in which the one or more posture loads are illustrated in time series. Furthermore, the load estimation apparatus stores posture loads of a plurality of measurement targets, extracts a posture load of a specific measurement target among the plurality of measurement targets, and displays display data relating to the specific measurement target.

Therefore, since the load estimation apparatus according to the second embodiment can perform load estimation for a plurality of workers, it is possible to perform comparison between the workers.

Third Embodiment

In the second embodiment, the description has been given of selecting a worker from a plurality of workers and performing load estimation for the selected worker. In a third embodiment, a description will be further given of selecting a load attribute and displaying a work section corresponding to the selected load attribute in a graph of posture load information.

Figure 22:
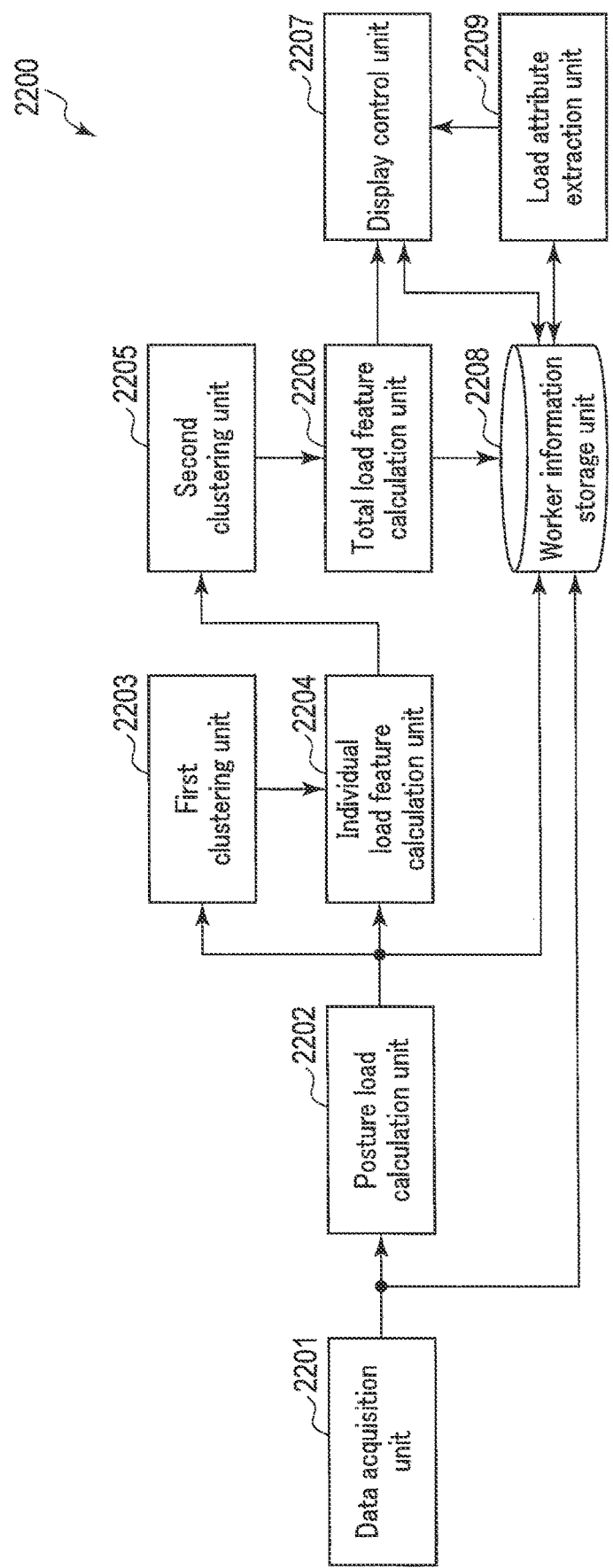
FIG. 22 is a block diagram illustrating a configuration of a load estimation apparatus according to a third embodiment.

FIG. 22 is a block diagram illustrating a configuration of a load estimation apparatus according to the third embodiment. A load estimation apparatus 2200 of FIG. 22 includes a data acquisition unit 2201, a posture load calculation unit 2202, a first clustering unit 2203 (first generation unit), an individual load feature calculation unit 2204, a second clustering unit 2205 (second generation unit), a total load feature calculation unit 2206, a display control unit 2207, a worker information storage unit 2208, and a load attribute extraction unit 2209.

Note that the data acquisition unit 2201, the posture load calculation unit 2202, the first clustering unit 2203, the individual load feature calculation unit 2204, the second clustering unit 2205, the total load feature calculation unit 2206, and the worker information storage unit 2208 have the same configurations as the data acquisition unit 1801, the posture load calculation unit 1802, the first clustering unit 1803, the individual load feature calculation unit 1804, the second clustering unit 1805, the total load feature calculation unit 1806, and the worker information storage unit 1808 in FIG. 18, and thus, description thereof is omitted.

The load attribute extraction unit 2209 accepts the selection of the load attribute from the user, and reads the worker information table from the worker information storage unit 2208. Then, the load attribute extraction unit 2209 extracts a time range corresponding to the selected load attribute from the worker information table. The load attribute extraction unit 2209 outputs information on the extracted time range to the display control unit 2207.

The display control unit 2207 receives the extracted time range from the load attribute extraction unit 2209. The display control unit 2207 displays display data in which the extracted time range is emphasized with respect to the posture load graph. Note that the display control unit 2207 may display the display data obtained by extracting one or more posture loads included in the extracted time range with respect to the posture load graph.

FIG. 23 is a flowchart illustrating an operation of the load estimation apparatus according to the third embodiment. The process of the flowchart of FIG. 23 is started, for example, after the process of the flowchart of FIG. 3 (after the process of Step S370) when the load estimation program is executed by the user. Note that the process of the flowchart of FIG. 23 may be performed simultaneously with the process of the flowchart of FIG. 19.
(Step S2310)

After the process of Step S370, the load estimation apparatus 100 accepts the selection of the load attribute from the user. At this time, the user can select the load attribute from a pull-down menu displayed in the display data to be described later.
(Step S2320)

After the load attribute is selected, the load attribute extraction unit 2209 reads the worker information table from the worker information storage unit 2208, and extracts a time range corresponding to the selected load attribute.
(Step S2330)

After the time range is extracted, the display control unit 2207 displays display data in which the extracted time range is emphasized with respect to the posture load graph. After the process of Step S2330, the process of the flowchart of FIG. 23 is ended.

FIG. 24 is an example of the display data in the third embodiment. Display data 2400 of FIG. 24 further includes a display area 2410 for the load attribute, with respect to the display data 2100 of FIG. 21. In the display area 2410, a pull-down menu 2411 in which load attributes are displayed and stored is displayed.

For example, in a case where the user selects the load attribute "waist load" from the pull-down menu 2411, the display control unit 2207 displays, in an emphasized manner, a time range in which the load is particularly large in the graph of the posture load relating to the waist. For example, in FIG. 24, a time range 2421, a time range 2422, and a time range 2423 are highlighted to be displayed in an emphasized manner. In particular, the load strength in the time range 2422 is higher than the load strength in the time range 2421 and the time range 2423. Therefore, the highlight in the time range 2422 is further emphasized than the highlights in the time range 2421 and the time range 2423.

As described above, the load estimation apparatus according to the third embodiment acquires sensor data from a measurement target, calculates one or more posture loads relating to one or more body parts of the measurement target based on the sensor data, and displays display data including a posture load graph in which the one or more posture loads are illustrated in time series. Furthermore, the load estimation apparatus performs first clustering of classifying the posture loads into a number of dimensions higher than the number of dimensions of the information on the posture loads to generate a first clustering result, performs second clustering of classifying the posture loads into a number of dimensions equal to or less than the number of dimensions of the first clustering based on the information on the posture loads and the first clustering result to generate a second clustering result, and calculates a total load feature relating to the measurement target based on the second clustering result. Further, the load estimation apparatus determines a load attribute relating to the load type for each cluster classified by the second clustering, and displays, in an emphasized manner, a time range corresponding to a specific load attribute among the plurality of load attributes on the posture load graph. Therefore, the load estimation apparatus according to the third embodiment can confirm the work period for each load attribute.

Fourth Embodiment

In the third embodiment, the description has been given of selecting a load attribute and displaying a work section corresponding to the selected load attribute in a graph of posture load information. On the other hand, in a fourth embodiment, a description will be given of selecting a work type and displaying a work section corresponding to the selected work type in a graph of posture load information.

FIG. 25 is a block diagram illustrating a configuration of a load estimation apparatus according to the fourth embodiment. A load estimation apparatus 2500 of FIG. 25 includes a data acquisition unit 2501, a posture load calculation unit 2502, a first clustering unit 2503 (first generation unit), an individual load feature calculation unit 2504, a second clustering unit 2505 (second generation unit), a total load feature calculation unit 2506, a display control unit 2507, a worker information storage unit 2508, a work type information storage unit 2509, and a work type extraction unit 2510.

Note that the data acquisition unit 2501, the posture load calculation unit 2502, the first clustering unit 2503, the individual load feature calculation unit 2504, the second clustering unit 2505, the total load feature calculation unit 2506, and the worker information storage unit 2508 have the same configurations as the data acquisition unit 1801, the posture load calculation unit 1802, the first clustering unit 1803, the individual load feature calculation unit 1804, the second clustering unit 1805, the total load feature calculation unit 1806, and the worker information storage unit 1808 in FIG. 18, and thus, description thereof is omitted.

The work type information storage unit 2509 stores a worker ID, a work type that is a type of work, and a work period in association with each other. Specifically, the work type information storage unit 2509 stores a work type information table in which a worker ID, a work type, a start time of a work period, and an end time of a work period are associated with each other. The work type information storage unit 2509 outputs the work type information table to the work type extraction unit 2510.

It is assumed that the work type and the work period are estimated based on, for example, the sensor data. Specifically, for example, the load estimation apparatus 100 may estimate a work type and a work period by using a learned model of machine learning learned to output the work type and the work period when the sensor data is input.

The work type extraction unit 2510 accepts the selection of a work type from the user, reads the worker information table from the worker information storage unit 2508, and reads the work type information table from the work type information storage unit 2509. Then, the work type extraction unit 2510 extracts a work period (time range) corresponding to the selected work type from the work type information table. The work type extraction unit 2510 outputs information on the extracted time range to the display control unit 2507.

The display control unit 2507 receives the extracted time range from the work type extraction unit 2510. The display control unit 2507 displays display data in which the extracted time range is emphasized with respect to the posture load graph. Note that the display control unit 2507 may display the display data obtained by extracting one or more posture loads included in the extracted time range with respect to the posture load graph.

Figures 26, 27:
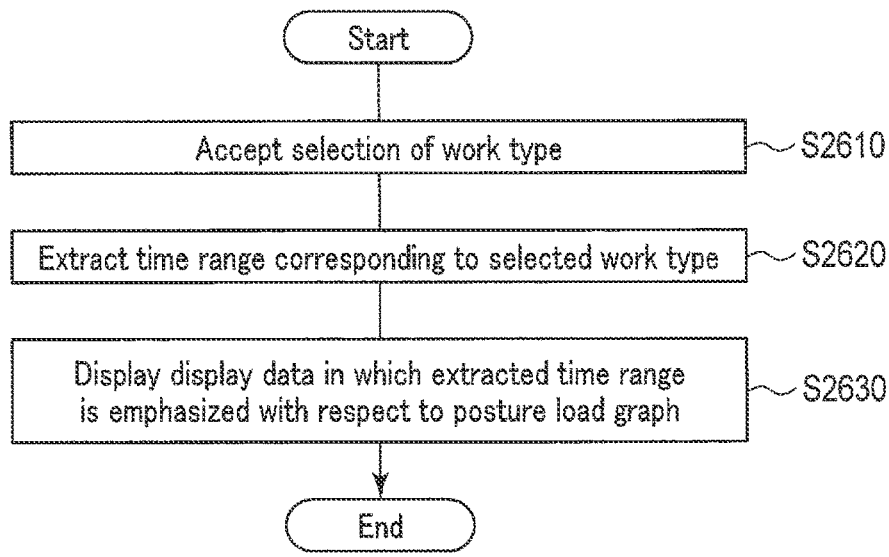
FIG. 26 is a flowchart illustrating an operation of the load estimation apparatus according to the fourth embodiment.
FIG. 27 is a table in which a worker ID, a work type, and a work period are associated with each other in the fourth embodiment.

FIG. 26 is a flowchart illustrating an operation of the load estimation apparatus according to the fourth embodiment. The process of the flowchart of FIG. 26 is started, for example, after the process of the flowchart of FIG. 3 (after the process of Step S370) when the load estimation program is executed by the user. Note that the process of the flowchart of FIG. 26 may be performed simultaneously with the process of the flowchart of FIG. 19.

(Step S2610)

After the process of Step S370, the load estimation apparatus 100 accepts the selection of the work type from the user. At this time, the user can select a work type from a pull-down menu displayed in display data to be described later.

(Step S2620)

After the work type is selected, the work type extraction unit 2510 reads the work type information table from the work type information storage unit 2509, and extracts a time range corresponding to the selected work type. A specific example of the work type information table will be described with reference to FIG. 27.

FIG. 27 is a table in which a worker ID, a work type, and a work period are associated with each other in the fourth embodiment. In a table 2700 (work type information table) of FIG. 27, a worker ID, a work type, and a work period (a start time and an end time) are associated with each other. In the table 2700, a work type in which work periods overlap may be included.

(Step S2630)

After the time range is extracted, the display control unit 2507 displays display data in which the extracted time range is emphasized with respect to the posture load graph. After the process of Step S2630, the process of the flowchart of FIG. 26 is ended.

FIG. 28 is an example of the display data in the fourth embodiment. Display data 2800 of FIG. 28 further includes a display area 2810 for the work type, with respect to the display data 2100 of FIG. 21. In the display area 2810, a pull-down menu 2811 in which the work types are displayed and stored is displayed.

For example, in a case where the user selects the work type "power supply installation" from the pull-down menu 2811, the display control unit 2507 emphasizes a time range corresponding to the power supply installation in the posture load graph of a part with a particularly large load in the posture load graph. For example, in FIG. 28, a time range 2821 in the posture load graph of the wrist and the posture load graph of the upper arm is highlighted to be displayed in an emphasized manner.

As described above, the load estimation apparatus according to the fourth embodiment acquires sensor data from a measurement target, calculates one or more posture loads relating to one or more body parts of the measurement target based on the sensor data, and displays display data including a posture load graph in which the one or more posture loads are illustrated in time series. Further, the load estimation apparatus stores a work type which is a type of work performed by the measurement target and a work period in association with each other, and displays, in an emphasized manner, a time range corresponding to a specific work type among a plurality of work types on the posture load graph. Therefore, the load estimation apparatus according to the fourth embodiment can confirm the work with a high load by focusing on the work period for each work type.

Fifth Embodiment

In the first to fourth embodiments, the load estimation is performed using the sensor data of the sensor attached to the worker. On the other hand, in a fifth embodiment, a description will be further given of specifying a work place by using video data using an imaging apparatus, and displaying work load information based on the work place.

FIG. 29 is a block diagram illustrating a configuration of a load estimation system including a load estimation apparatus according to the fifth embodiment. A load estimation system 1A of FIG. 29 includes a load estimation apparatus 100A, an output apparatus 110, one or more sensors, and an imaging apparatus 2900. In FIG. 29, a first sensor 121, a second sensor 122, and a third sensor 123 are illustrated as one or more sensors. These sensors are similar to the one or more sensors of FIG. 1. The load estimation apparatus 100A estimates a load characteristic based on one or more pieces of sensor data and video data.

The imaging apparatus 2900 is, for example, a video camera. The imaging apparatus 2900 captures an image of a work place (for example, an assembly work site in a factory, and the like) where a worker is working, and acquires a still image or a moving image. In the embodiment, a still image or a moving image acquired by the imaging apparatus 2900 is referred to as video data. The imaging apparatus 2900 outputs the acquired video data to the load estimation apparatus 100A. The video data may include a shooting time.

FIG. 30 is a block diagram illustrating a configuration of the load estimation apparatus according to the fifth embodiment. The load estimation apparatus 100A of FIG. 30 includes a data acquisition unit 3001, a posture load calculation unit 3002, a first clustering unit 3003 (first generation unit), an individual load feature calculation unit 3004, a second clustering unit 3005 (second generation unit), a total load feature calculation unit 3006, a display control unit 3007, a worker information storage unit 3008, a video data acquisition unit 3009, a place information storage unit 3010, a work place specification unit 3011, and a place-specific load estimation unit 3012.

Note that the data acquisition unit 3001, the posture load calculation unit 3002, the first clustering unit 3003, the individual load feature calculation unit 3004, the second clustering unit 3005, the total load feature calculation unit 3006, and the worker information storage unit 3008 have the same configurations as the data acquisition unit 1801, the posture load calculation unit 1802, the first clustering unit 1803, the individual load feature calculation unit 1804, the second clustering unit 1805, the total load feature calculation unit 1806, and the worker information storage unit 1808 in FIG. 18, and thus, description thereof is omitted.

The video data acquisition unit 3009 acquires video data from the imaging apparatus 2900. The video data acquisition unit 3009 outputs the acquired video data to the work place specification unit 3011. The video data acquisition unit 3009 may acquire video data from a storage unit in which video data captured by the imaging apparatus 2900 is stored in advance. In addition, the video data acquisition unit 3009 may be included in the data acquisition unit 3001. In this case, the data acquisition unit 3001 acquires the video data.

The place information storage unit 3010 stores a sketch (map) of a work place. Specifically, the place information storage unit 3010 stores a sketch corresponding to the installation position of the imaging apparatus 2900. The place information storage unit 3010 outputs a sketch of the work place to the work place specification unit 3011. Area information obtained by dividing a work place into a plurality of work areas may be associated with the sketch.

The work place specification unit 3011 receives the video data from the video data acquisition unit 3009, and receives a sketch of the work place from the place information storage unit 3010. The work place specification unit 3011 specifies a work place (alternatively, a work area) of the worker based on the video data. The work place specification unit 3011 outputs information on the specified work place (work place information) to the place-specific load estimation unit 3012.

Specifically, the work place specification unit 3011 detects the worker from the video data. For the worker detection, for example, image recognition techniques such as a background subtraction method, a human body detection technique, a skeleton extraction technique, and a face detection technique are used.

Next, the work place specification unit 3011 specifies the position of the worker on the sketch. Specifically, the work place specification unit 3011 specifies the position (for example, coordinates of the foot of the worker) of the worker in the video data. Next, the work place specification unit 3011 assumes a three-dimensional space with the sketch as a floor surface, and perspectively projects the video data on the plane of the sketch with the camera position in the three-dimensional space as a starting point. Then, the work place specification unit 3011 specifies the position of the worker on the sketch by associating the position of the worker in the projected video data with the coordinates of the sketch.

Furthermore, the work place specification unit 3011 may specify the time during which the worker has been working, for each of the plurality of work areas set on the sketch. In this case, the work place information includes, for example, data in which work time is associated with each of the plurality of work areas.

The place-specific load estimation unit 3012 receives the posture load information from the worker information storage unit 3008, and receives the specified work place information from the work place specification unit 3011. The place-specific load estimation unit 3012 calculates a work load (place-specific load) for each work area by integrating or averaging the work loads for the work time for each of the plurality of work areas included in the work place information. The place-specific load estimation unit 3012 outputs information on the calculated place-specific load (place-specific load information) to the display control unit 3007.

The display control unit 3007 receives the place-specific load information from the place-specific load estimation unit 3012. The display control unit 3007 generates a graph visualizing the work load for each work area based on the place-specific load information. The graph here is represented by, for example, a pie chart.

The display control unit 3007 displays display data including the posture load graph and the generated graph (pie chart). Further, the display control unit 3007 may display the display data including the video data, or may display the display data including the posture load graph and the video data.

FIG. 31 is a flowchart illustrating an operation of the load estimation apparatus according to the fifth embodiment. The process of the flowchart of FIG. 31 is started, for example, after the process of the flowchart of FIG. 3 (after the process of Step S370) when the load estimation program is executed by the user. Note that the process of the flowchart of FIG. 31 may be performed simultaneously with the process of the flowchart of FIG. 19.

(Step S3110)

After the process of Step S370, the video data acquisition unit 3009 acquires video data.

Figure 32:
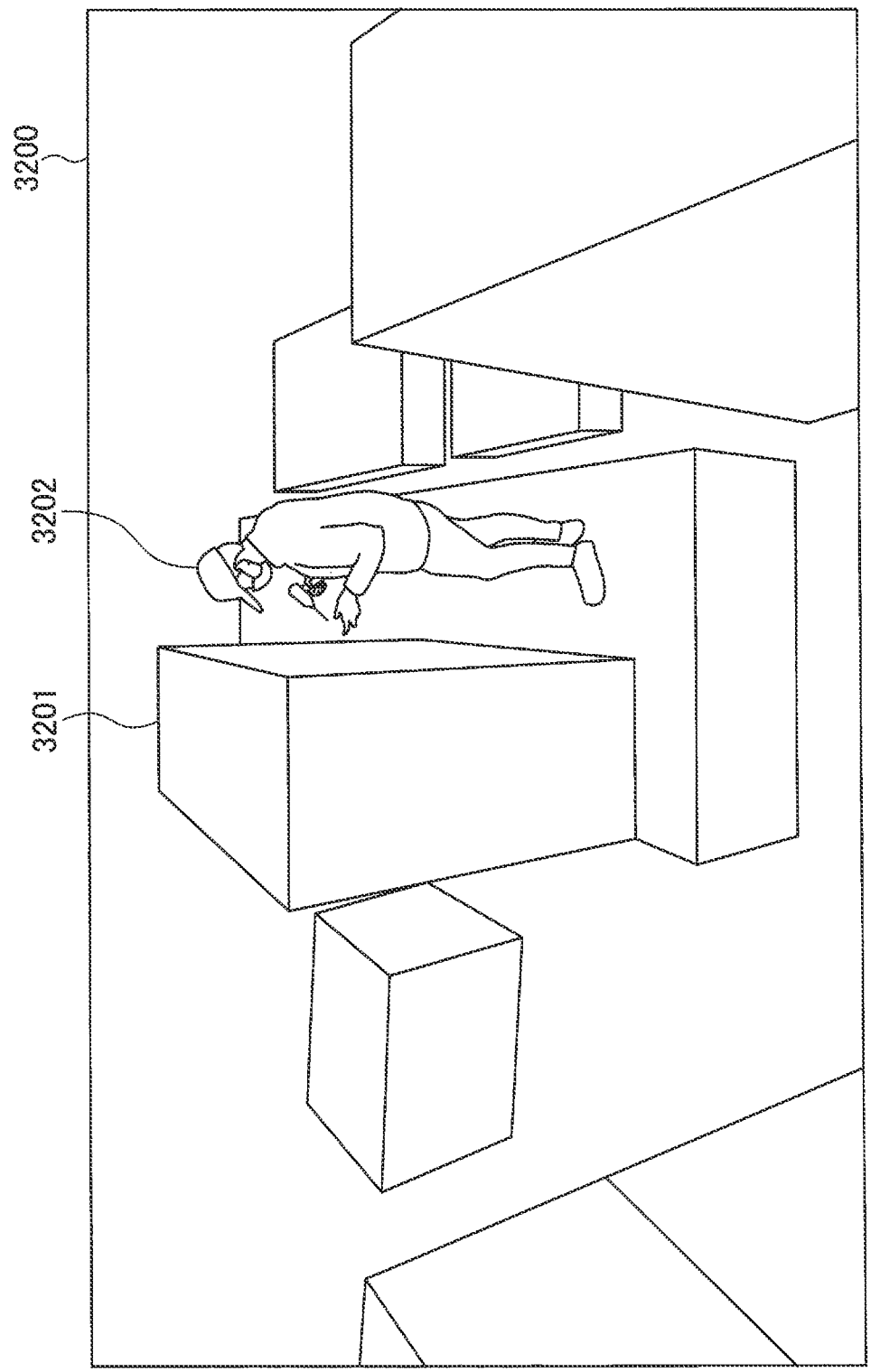
FIG. 32 is a diagram illustrating an image of video data in the fifth embodiment.

FIG. 32 is a diagram illustrating an image of the video data in the fifth embodiment. An image 3200 of FIG. 32 is obtained by imaging a work place. The work place includes, for example, a product 3201. In the image 3200, a worker 3202 in the work place is shown. The worker 3202 is working on the right of the product 3201.

(Step S3120)

After the video data is acquired, the work place specification unit 3011 specifies the work place of the worker based on the video data. Specifically, the work place specification unit 3011 detects the worker from the video data, and specifies the position of the worker on the sketch.

Figure 33:
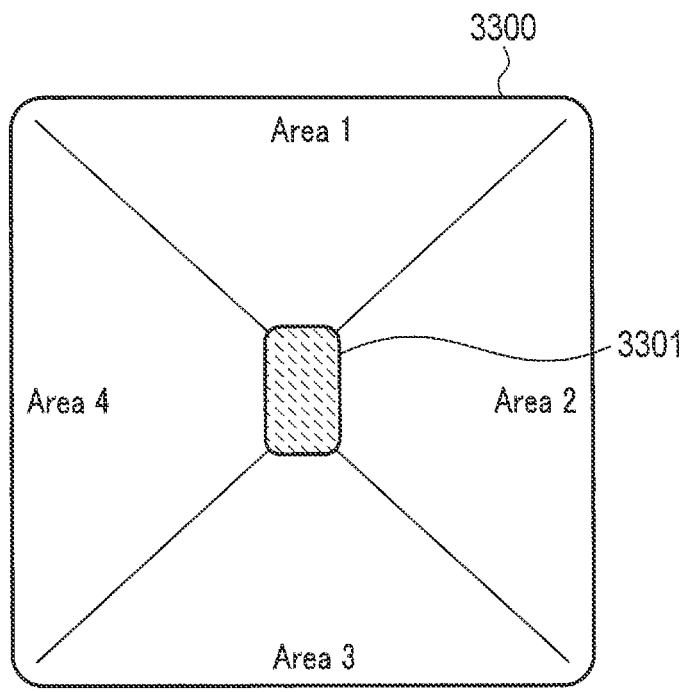
FIG. 33 is a diagram illustrating a two-dimensional sketch in the fifth embodiment.

FIG. 33 is a diagram illustrating a sketch in the fifth embodiment. A sketch 3300 of FIG. 33 is a bird's-eye view of a work place viewed from the above. In the sketch 3300, a product 3301 corresponding to the product 3201 located at the work place of FIG. 32 is shown.

The sketch 3300 is divided into four work areas (an area 1, an area 2, an area 3, and an area 4) around the product 3201. The area 1 corresponds to an upper region of the product 3201, the area 2 corresponds to a right region of the product 3201, the area 3 corresponds to a lower region of the product 3201, and the area 4 corresponds to a left region of the product 3201.

Figure 34:
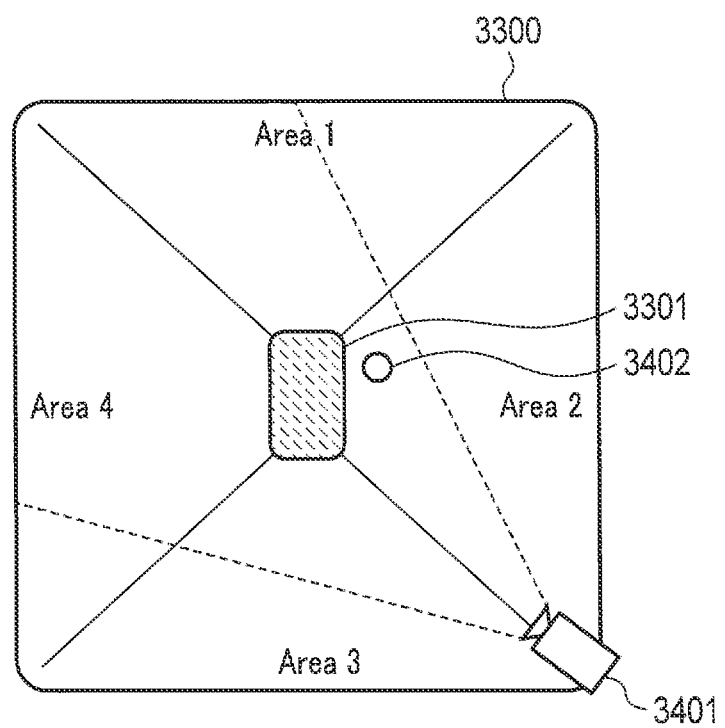
FIG. 34 is a diagram illustrating an imaging apparatus and a worker displayed on the sketch of FIG. 33.

FIG. 34 is a diagram illustrating an imaging apparatus and a worker displayed on the sketch of FIG. 33. In the sketch 3300 of FIG. 34, an imaging apparatus 3401 is displayed between the area 2 and the area 3, and a worker 3402 is displayed in the area 2. The position of the worker 3402 on the sketch 3300 is changed in accordance with the position of the worker of the video data.

(Step S3130)

After the work place of the worker is specified, the display control unit 3007 displays display data based on the specified work place (work area). Specifically, the display control unit 3007 generates a pie chart that visualizes the work load for each work area. Then, the display control unit 3007 displays the display data including the generated pie chart.

FIG. 35 is a diagram illustrating pie charts displayed together with the sketch in the fifth embodiment. FIG. 35 illustrates a pie chart 3501, a pie chart 3502, a pie chart 3503, and a pie chart 3504 respectively corresponding to the area 1 to the area 4 in the sketch. The size of the pie chart corresponds to an integrated value or an average value of the work loads. The ratio of the pie chart is the ratio of the load characteristic (load strength) for each part.

Since the ratio of the load strength of the waist is higher than other parts in the pie chart 3501, an attribute of "high ratio of 'waist load'" is added to the pie chart 3501. Since the pie chart 3502 is larger than the other pie charts and the ratio of the load strength of the arm occupies most of the pie chart 3502, an attribute of "'arm load large' dominant" is added to the pie chart 3502. Since the ratio of the load strength of the waist occupies most of the pie chart 3503, an attribute of "'waist load' dominant" is added to the pie chart 3503. Since the ratio of the load strength of the wrist is higher than other parts in the pie chart 3504, an attribute of "high ratio of 'wrist load'" is added to the pie chart 3504.

Figure 36:
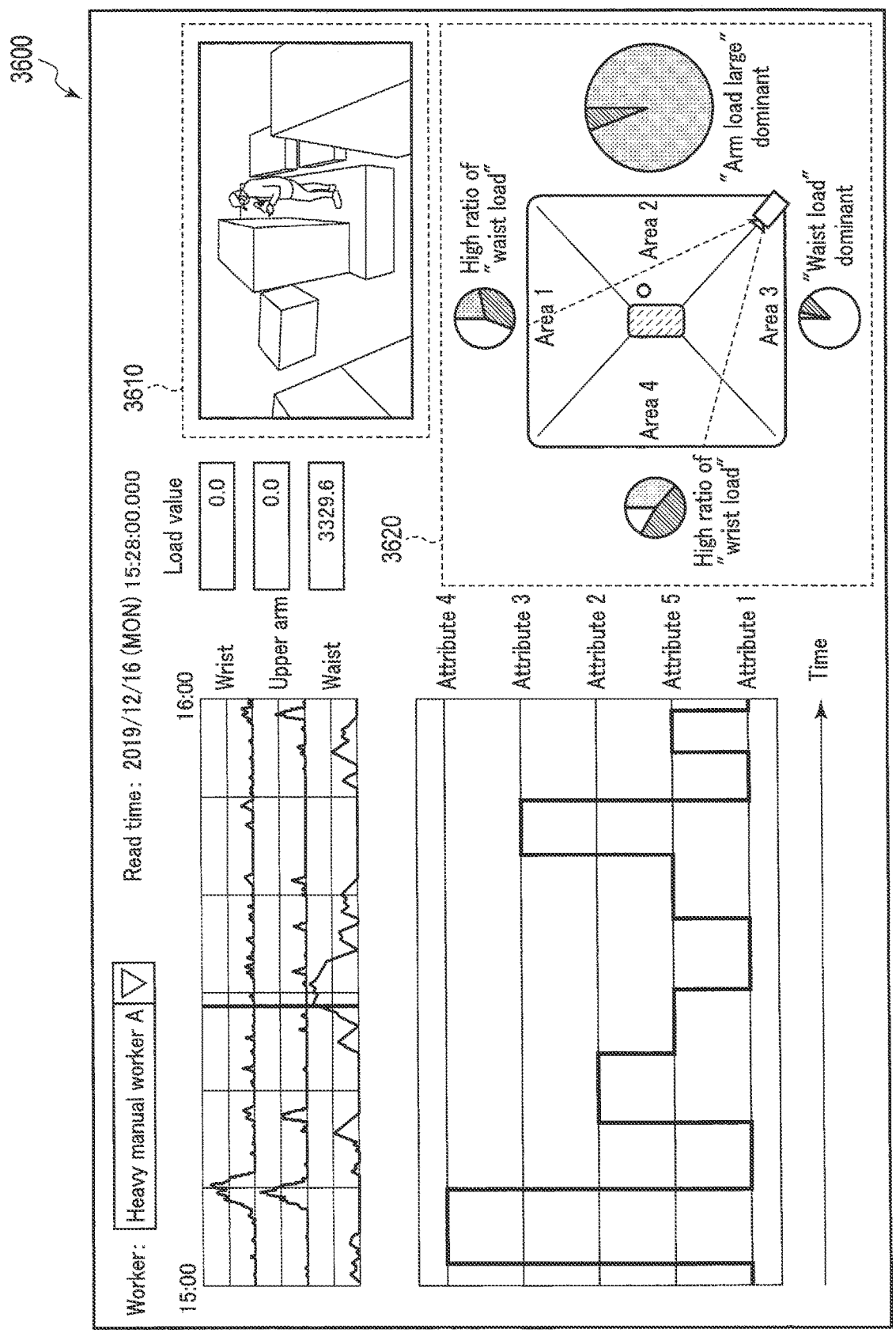
FIG. 36 is an example of display data in the fifth embodiment.

FIG. 36 is an example of the display data in the fifth embodiment. Display data 3600 of FIG. 36 further includes a display area 3610 for the image of the video data and a display area 3620 for the sketch and the pie chart, with respect to the display data 2100 of FIG. 21. In the display area 3610, for example, the image 3200 of FIG. 32 is displayed. In the display area 3620, for example, the sketch and four pie charts of FIG. 35 are displayed.

As described above, the load estimation apparatus according to the fifth embodiment acquires sensor data from a measurement target, calculates one or more posture loads relating to one or more body parts of the measurement target based on the sensor data, and displays display data including a posture load graph in which the one or more posture loads are illustrated in time series. Furthermore, the load estimation apparatus acquires video data of a work place including a measurement target, stores a map of the work place and area information obtained by dividing the map into one or more areas in association with each other, specifies the work place based on the video data, calculates a work load for each of a plurality of work areas included in the work place, and displays display data including a graph visualizing the work load for each of the plurality of work areas. Further, the load estimation apparatus may display the display data including video data.

Since the load estimation apparatus according to the fifth embodiment can quantitatively grasp different work loads for each work area, it is possible to consider measures for improvement by focusing on the work area with the high work load. Furthermore, since the load estimation apparatus can also confirm the video data for the work area with the high work load, it is possible to grasp a more specific work situation.

FIG. 37 is a block diagram illustrating a hardware configuration of a computer according to an embodiment. A computer 3700 includes, as hardware, a central processing unit (CPU) 3710, a random access memory (RAM) 3720, a program memory 3730, an auxiliary storage apparatus 3740, and an input/output interface 3750. The CPU 3710 communicates with the RAM 3720, the program memory 3730, the auxiliary storage apparatus 3740, and the input/output interface 3750 via a bus 3760.

The CPU 3710 is an example of a general-purpose processor. The RAM 3720 is used as a working memory for the CPU 3710. The RAM 3720 includes a volatile memory such as a synchronous dynamic random access memory (SDRAM). The program memory 3730 stores various programs including a load estimation program. As the program memory 3730, for example, a read-only memory (ROM), a part of the auxiliary storage apparatus 3740, or a combination thereof is used.

The auxiliary storage apparatus 3740 non-temporarily stores data. The auxiliary storage apparatus 3740 includes a nonvolatile memory such as an HDD or an SSD.

The input/output interface 3750 is an interface for the connection or communication with another device. The input/output interface 3750 is used, for example, for the connection or communication with the output apparatus 110, the first sensor 121, the second sensor 122, and the third sensor 123 which are illustrated in FIGS. 1 and 29, and the imaging apparatus 2900 illustrated in FIG. 29.

Each program stored in the program memory 3730 includes a computer-executable instruction. When the program (computer-executable instruction) is executed by the CPU 3710, the program causes the CPU 3710 to execute a predetermined process. For example, when the load estimation program is executed by the CPU 3710, the load estimation program causes the CPU 3710 to execute a series of processes described for each unit of FIGS. 3, 4, 19, 23, 26, and 31.

The program may be provided to the computer 3700 in a state of being stored in a computer-readable storage medium. In this case, for example, the computer 3700 further includes a drive (not illustrated) that reads data from the storage medium, and acquires the program from the storage medium. Examples of the storage medium include a magnetic disk, an optical disk (CD-ROM, CD-R, DVD-ROM, DVD-R, or the like), a magneto-optical disk (MO or the like), and a semiconductor memory. In addition, the program may be stored in a server on a communication network, and the computer 3700 may download the program from the server using the input/output interface 3750.

The process described in the embodiments is not limited to being performed by a general-purpose hardware processor such as the CPU 3710 executing a program, and may be performed by a dedicated hardware processor such as an application specific integrated circuit (ASIC). The term processing circuit (processing unit) includes at least one general-purpose hardware processor, at least one dedicated hardware processor, or a combination of at least one general-purpose hardware processor and at least one dedicated hardware processor. In the example illustrated in FIG. 37, the CPU 3710, the RAM 3720, and the program memory 3730 correspond to a processing circuit.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A load estimation apparatus comprising a hardware processor configured to:
   acquire sensor data from a measurement target;
   calculate one or more posture loads relating to one or more body parts of the measurement target based on the sensor data;
   perform, using information on the posture loads, first clustering of classifying the posture loads into a number of dimensions higher than the number of dimensions of the information on the posture loads to generate a first clustering result;
   perform, using a distance from a representative sample in each cluster included in the first clustering result to each of a plurality of samples included in the information on the posture loads, second clustering of classifying the posture loads into a number of dimensions equal to or less than the number of dimensions of the first clustering to generate a second clustering result;

calculate a total load feature relating to the measurement target based on the second clustering result; and and display display data including a posture load graph in which the calculated one or more posture loads are illustrated in time series and a graph based on the calculated total load feature.

2. The load estimation apparatus according to claim 1, wherein the hardware processor is further configured to calculate the posture load based on a distribution of posture angles of the body part.

3. The load estimation apparatus according to claim 1, wherein the hardware processor is further configured to:
store posture loads of a plurality of measurement targets;
extract a posture load of a specific measurement target among the measurement targets; and
display display data relating to the specific measurement target.

4. The load estimation apparatus according to claim 1, wherein the first clustering result includes data in which a sample ID and a first cluster ID are associated with each other, and information on the representative sample in each cluster, the sample ID is assigned to each of the plurality of samples included in the information on the posture load, the first cluster ID is for distinguishing each cluster classified by the first clustering, and the hardware processor is further configured to:
calculate an individual load feature in which a distance between the sample and each of the representative samples is associated for each of the samples based on the information on the posture load and the first clustering result; and
perform the second clustering based on the information on the individual load feature to generate the second clustering result.

5. The load estimation apparatus according to claim 4, wherein the second clustering result includes data in which the sample ID and a second cluster ID are associated with each other, the second cluster ID is for distinguishing each cluster classified by the second clustering and the hardware processor is further configured to determine a load attribute relating to a load type of a cluster for the second cluster ID.

6. The load estimation apparatus according to claim 5, wherein the total load feature includes data in which the second cluster ID and the load attribute are associated with each other, and the hardware processor is further configured to:
extract a time range corresponding to a specific load attribute among a plurality of load attributes; and
display the display data in which the time range is emphasized with respect to the posture load graph.

7. The load estimation apparatus according to claim 1, wherein the hardware processor is further configured to:
store a work type and a work period in association with each other, the work type is a type of work performed by the measurement target;
extract a time range corresponding to a specific work type among a plurality of work types; and
display the display data in which the time range is emphasized with respect to the posture load graph.

8. The load estimation apparatus according to claim 1, wherein the hardware processor is further configured to:
acquire video data of a work place including the measurement target; and
display the display data further including the video data.

9. The load estimation apparatus according to claim 1, wherein the hardware processor is further configured to:
acquire video data of a work place including the measurement target;
store a map of the work place and area information in association with each other, the area information is obtained by dividing the map into one or more areas;
specify the work place based on the video data;
calculate a work load for each of a plurality of work areas included in the work place; and
display the display data including a graph visualizing the work load for each of the work areas.

10. The load estimation apparatus according to claim 9, wherein the hardware processor is further configured to display the display data further including the video data.

11. A load estimation method comprising:
acquiring sensor data from a measurement target;
calculating one or more posture loads relating to one or more body parts of the measurement target based on the sensor data;
performing, using information on the posture loads, first clustering of classifying the posture loads into a number of dimensions higher than the number of dimensions of the information on the posture loads to generate a first clustering result;
performing, using a distance from a representative sample in each cluster included in the first clustering result to each of a plurality of samples included in the information on the posture loads, second clustering of classifying the posture loads into a number of dimensions equal to or less than the number of dimensions of the first clustering to generate a second clustering result;
calculating a total load feature relating to the measurement target based on the second clustering result; and
displaying display data including a posture load graph in which the calculated one or more posture loads are illustrated in time series and a graph based on the calculated total load feature.

* * * * *